US009051570B2

(12) United States Patent
Wengel

(10) Patent No.: US 9,051,570 B2
(45) Date of Patent: *Jun. 9, 2015

(54) UNA OLIGOMERS FOR THERAPEUTICS

(71) Applicant: Arcturus Therapeutics, Inc., San Diego, CA (US)

(72) Inventor: Jesper Wengel, Odense C (DK)

(73) Assignee: Arcturus Therapeutics, Inc., San Diego, CA (US)

( * ) Notice: Subject to any disclaimer, the term of this patent is extended or adjusted under 35 U.S.C. 154(b) by 153 days.

This patent is subject to a terminal disclaimer.

(21) Appl. No.: 13/652,965

(22) Filed: Oct. 16, 2012

(65) Prior Publication Data

US 2013/0096289 A1  Apr. 18, 2013

Related U.S. Application Data

(63) Continuation of application No. 12/515,403, filed as application No. PCT/US2008/064417 on May 21, 2008, now Pat. No. 8,314,227.

(30) Foreign Application Priority Data

| May 22, 2007 | (DK) | ................................ | 2007 00751 |
| Nov. 30, 2007 | (DK) | ................................ | 2007 01718 |
| Dec. 14, 2007 | (DK) | ................................ | 2007 01785 |
| Apr. 20, 2008 | (DK) | ................................ | 2008 00534 |

(51) Int. Cl.
| *C07H 21/04* | (2006.01) |
| *C12N 15/113* | (2010.01) |
| *C07H 21/00* | (2006.01) |
| *C12N 15/11* | (2006.01) |

(52) U.S. Cl.
CPC .............. *C12N 15/113* (2013.01); *C07H 21/00* (2013.01); *C12N 15/111* (2013.01); *C12N 2310/14* (2013.01); *C12N 2310/323* (2013.01); *C12N 2320/51* (2013.01)

(58) Field of Classification Search
CPC .......................... C12N 15/113; C12N 2320/51
See application file for complete search history.

(56) References Cited

U.S. PATENT DOCUMENTS

| 4,199,574 | A | 4/1980 | Schaeffer |
| 4,968,686 | A | 11/1990 | Townsend |
| 5,786,359 | A | 7/1998 | Reitz |
| 5,898,031 | A | 4/1999 | Crooke |
| 6,037,176 | A | 3/2000 | Bennett |
| 6,069,132 | A | 5/2000 | Revanker |
| 6,506,559 | B1 | 1/2003 | Fire |
| 6,608,035 | B1 | 8/2003 | Agrawal |
| 6,753,139 | B1 | 6/2004 | Baulcombe |
| 7,056,704 | B2 | 6/2006 | Tuschl |
| 7,078,196 | B2 | 7/2006 | Tuschl |
| 7,459,547 | B2 | 12/2008 | Zamore |
| 7,579,451 | B2 | 8/2009 | Manoharan |
| 7,691,995 | B2 | 4/2010 | Zamore |
| 7,745,608 | B2 | 6/2010 | Manoharan |
| 7,750,144 | B2 | 7/2010 | Zamore |
| 7,786,290 | B2 | 8/2010 | Woppmann |
| 7,915,399 | B2 | 3/2011 | MacLachlan |
| 8,101,584 | B2 | 1/2012 | Kreutzer |
| 8,101,742 | B2 | 1/2012 | Kreutzer |
| 8,258,285 | B2 | 9/2012 | Baulcombe |
| 8,314,227 | B2 * | 11/2012 | Wengel ........................ 536/24.5 |
| 8,362,231 | B2 | 1/2013 | Tuschl |
| 8,420,391 | B2 | 4/2013 | Tuschl |
| 8,546,143 | B2 | 10/2013 | Kreutzer |
| 2002/0086356 | A1 | 7/2002 | Tuschl |
| 2003/0143732 | A1 | 7/2003 | Fosnaugh |
| 2004/0171570 | A1 | 9/2004 | Allerson |
| 2004/0175703 | A1 | 9/2004 | Kreutzer |
| 2004/0192626 | A1 | 9/2004 | McSwiggen |
| 2004/0259247 | A1 | 12/2004 | Tuschl |
| 2005/0100907 | A1 | 5/2005 | Kreutzer |
| 2005/0107325 | A1 | 5/2005 | Manoharan |
| 2005/0223427 | A1 | 10/2005 | Khvorova |
| 2005/0244858 | A1 | 11/2005 | Rossi |
| 2005/0288244 | A1 | 12/2005 | Manoharan |
| 2006/0122391 | A1 | 6/2006 | Babu |
| 2006/0276635 | A1 | 12/2006 | McSwiggen |
| 2006/0287260 | A1 | 12/2006 | Manoharan |
| 2007/0275914 | A1 | 11/2007 | Manoharan |
| 2009/0093438 | A1 | 4/2009 | McSwiggen et al. |

FOREIGN PATENT DOCUMENTS

| WO | WO/96/29336 A1 | 9/1996 |
| WO | WO/99/08688 A1 | 2/1999 |
| WO | WO/03/004602 A2 | 1/2003 |

(Continued)

OTHER PUBLICATIONS

Pandolfi, Nucleosides & Nucleotides, 1999, vol. 18 (9), 2051-2069.
Habus, Nucleosides & Nucleotides, 1995, vol. 14 (9&10), 1853-1859.
IUPAC-IUB Joint Commission on Biochemical Nomenclature Abbreviations and Symbols for the Description of Conformations of Polynucleotide Chains, Current Protocols in Nucleic Acid Chemistry 2000, pp. A.1C.1-A.1D.3.

(Continued)

*Primary Examiner* — Jon E Angell

(74) *Attorney, Agent, or Firm* — Eckman Basu LLP

(57) ABSTRACT

This invention is directed to oligomers composed of 2'-3'-seco-nucleomonomers and nucleotides or modified nucleotides, wherein the oligomer can be a microRNA and include from one to five 2'-3'-seco-nucleomonomers. The oligomers can have a sequence that is complementary to a target nucleotide sequence and be used for affecting the regulation of gene expression. Among other things, the oligomers can provide reduced off target effects.

9 Claims, 7 Drawing Sheets

(56) References Cited

FOREIGN PATENT DOCUMENTS

| WO | 03037909 | A1 | 5/2003 |
|---|---|---|---|
| WO | WO/03/037909 | A1 | 5/2003 |
| WO | 03070918 | A2 | 8/2003 |
| WO | 03106477 | A1 | 12/2003 |
| WO | 2004090108 | A2 | 10/2004 |
| WO | WO2004090105 | A2 | 10/2004 |
| WO | WO/2004/094595 | A2 | 11/2004 |
| WO | 2005089268 | | 9/2005 |
| WO | 2005089287 | A2 | 9/2005 |
| WO | WO/2005/089268 | A2 | 9/2005 |
| WO | 2005121372 | A2 | 12/2005 |
| WO | 2006085987 | A2 | 8/2006 |
| WO | WO/2006/112872 | A2 | 10/2006 |
| WO | 2007022369 | A2 | 2/2007 |
| WO | 2007051303 | A1 | 5/2007 |

OTHER PUBLICATIONS

Mangos, Journal of the American Chemical Society, 2003, vol. 125, pp. 654-661, Efficient RNase H-Directed Cleavage of RNA Promoted by Antisense DNA or 2'F-ANA Constructs Containing Acyclic Nucleotide Inserts.

Nielsen, Bioorganic & Medicinal Chemistry,1995, vol. 3 (1), pp. 19-28, Synthesis and Evaluation of Oligodeoxynucleotides Containing Acyclic Nucleosides: Introduction of Three Novel Analogues and a Summary.

Thrane, Tetrahedron,1995, vol. 51 (37), pp. 10389-10402, Novel Linear and Branched Oligodeoxynucleotide Analogues Containing 4'-C-(Hydroxymethyl Thymidine.

Elbashir, EMBO Journal, 2001, vol. 20 (23), 6877-6888.

Czauderna, Nucleic Acids Research, 2003, vol. 31 (11), 2705-2716.

Nielsen, Oligonucleotide Analogues Containing 4'-C-(Hydroxymethyl)uridine: Synthesis, Evaluation and Mass Spectrometric Analysis, Bioorganic & Medicinal Chemistry, vol. 3, No. 1 I, pp. 1493-1502, 1995.

Petersen, LNA: a versatile tool for therapeutics and genomics, Trends in Biotechnology vol. 21 No. 2 Feb. 2003.

Pfundheller, Locked Nucleic Acid Synthesis, Chapter 8 in Methods in Molecular Biology, 2005, vol. 288: Oligonucleotide Synthesis: Methods and Applications, Edited by: P. Herdewijn, Humana Press.

* cited by examiner

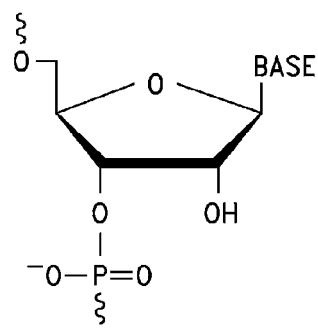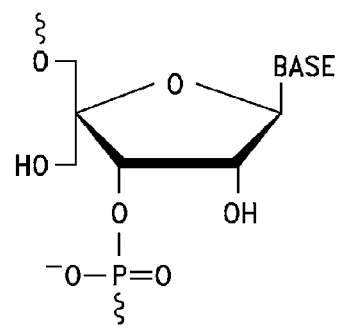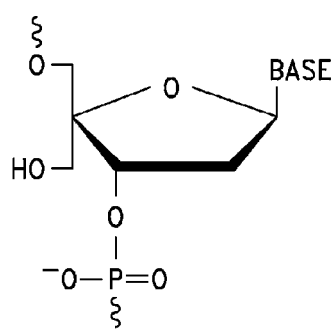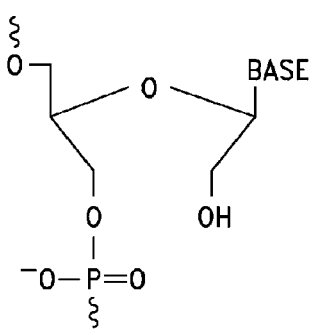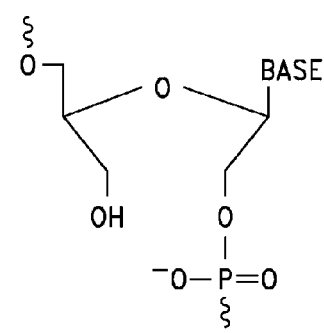
Fig. 1

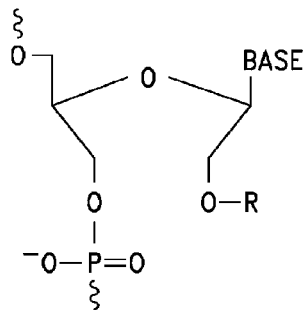
Monomer F
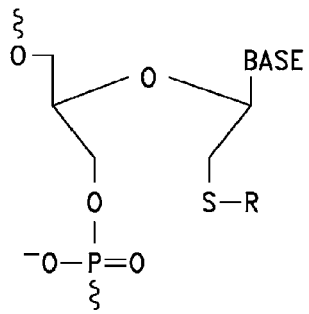
Monomer G
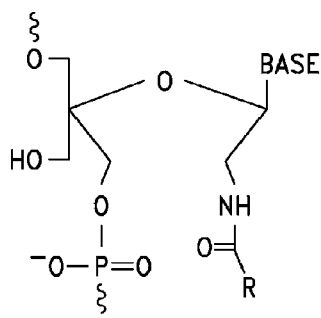
Monomer H
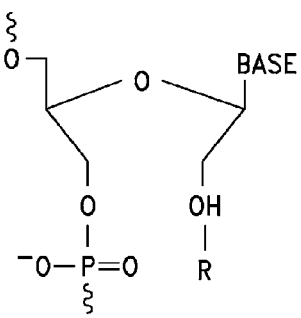
Monomer I
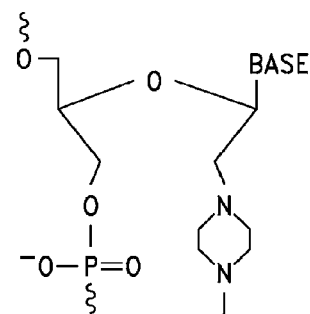
Monomer J
R = hydrogen, alkyl, cholesteryl derivative, fluorodphore, polyamine, fatty acid, amino acid, saccharide, or polypeptide
*Fig. 2*

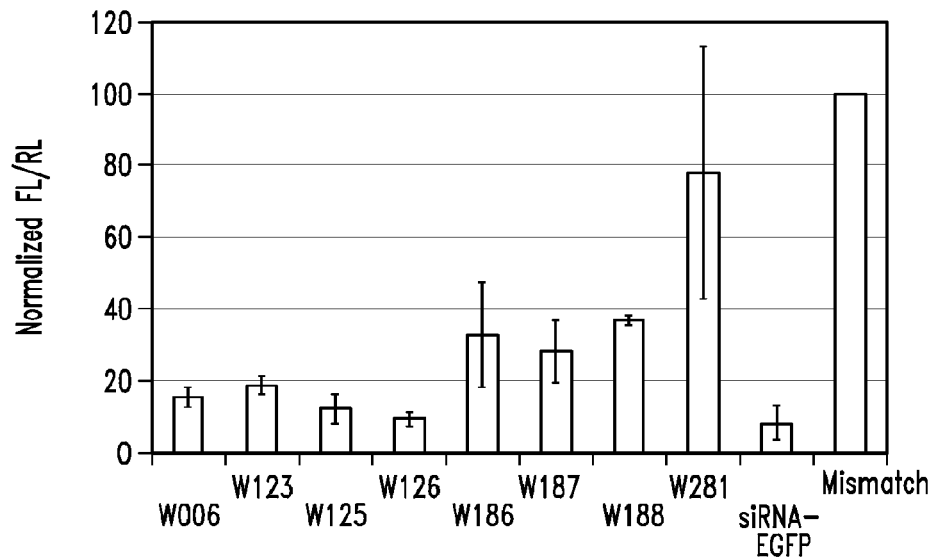

Antisense Strand W006: 5' - ACUUGUGGCCGUUUACGUCG$^L$C$^L$U (SEQ ID NO: 1)
Antisense Strand W123: 5' - ACUUGXGGCCGUUUACGUCG$^L$C$^L$U (SEQ ID NO: )
Antisense Strand W125: 5' - ACUUGUGGCCGUUUACGXCG$^L$C$^L$U (SEQ ID NO: )
Antisense Strand W126: 5' - ACUUGUGGCCGXUUACGUCG$^L$C$^L$U (SEQ ID NO: )
Antisense Strand W186: 5' - ACUUGXGGCCGXUUACGXCG$^L$C$^L$U (SEQ ID NO: )
Antisense Strand W187: 5' - ACUUGXGGCCGXUUACGUCG$^L$C$^L$U (SEQ ID NO: )
Antisense Strand W188: 5' - ACT$^L$UGT$^L$GGCCGXUT$^L$CACGT$^L$CG$^L$C$^L$U (SEQ ID NO: 4)
Antisense Strand W281: 5' - ACUUGUXGCCGUUUXCGUCGXU(SEQ ID NO: )
Sense Strand W130: 5' - GACGXAAACXGCCACAAGGUT$^L$C$^L$U (SEQ ID NO: )

Fig. 4

Sense Strand W131: 5' - ACGUAAACGGCCACAAGUUXU (SEQ ID NO:)

Sense Strand W282: 5' - GAXGUAAACGGCCACAXGUUXU (SEQ ID NO: 11)

Sense Strand W194: 5' - GACGUAAACGGCCACAAGGUT$^L$C$^L$U (SEQ ID NO: )

Sense Strand W181: 5' - GAC$^L$GUAAAC$^L$GGCC$^L$AC$^L$AAGGUT$^L$C$^L$(SEQ ID NO: )

SEQUENCE LISTING

```
<160> NUMBER OF SEQ ID NOS: 25

<210> SEQ ID NO 1
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 1
acuuguggcc guuuacgucg cu                                               22

<210> SEQ ID NO 2
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 2
acuuguggcc guuuacgucg cu                                               22

<210> SEQ ID NO 3
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 3
acuugtggcc guuuacgucg cu                                               22

<210> SEQ ID NO 4
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 4
actugtggcc guutacgtcg cu                                               22
```

```
<210> SEQ ID NO 5
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 5
acuuguggcc guuuacgucg cu                                              22

<210> SEQ ID NO 6
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 6
acuuguggcc guuuacgucg cu                                              22

<210> SEQ ID NO 7
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 7
acuuguggcc guuuacgucg cu                                              22

<210> SEQ ID NO 8
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 8
acuuguggcc guuuacgucg cu                                              22

<210> SEQ ID NO 9
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 9
acuuguggcc guuuacgtcg uu                                              22

<210> SEQ ID NO 10
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 10
acuuguggcc guuuacgtcg uu                                              22

<210> SEQ ID NO 11
<211> LENGTH: 22
<212> TYPE: DNA
<213> ORGANISM: Artificial sequence
<220> FEATURE:
```

```
<223> OTHER INFORMATION: Synthetic oligonucleotide

<400> SEQUENCE: 11
gacguaaacg gccacaaguu cu                                              22

<210> SEQ ID NO 12
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 12
gacguaaacg gccacaagut cu                                              22

<210> SEQ ID NO 13
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 13
gacguaaacg gccacaagut cu                                              22

<210> SEQ ID NO 14
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 14
gacguaaacg gccacaagtt c                                               21

<210> SEQ ID NO 15
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 15
gacguaaacg gccacaagut cu                                              22

<210> SEQ ID NO 16
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 16
gacgtaaacg gccacaagut cu                                              22

<210> SEQ ID NO 17
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 17
gacgtaaacg gccacaagtt c                                               21
```

-continued

```
<210> SEQ ID NO 18
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 18
gacguaaacg gccacaagut cu                                              22

<210> SEQ ID NO 19
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 19
gacguaaacu ggccacaagu tcu                                             23

<210> SEQ ID NO 20
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 20
gacguaaacg gccacaaguu uu                                              22

<210> SEQ ID NO 21
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 21
gacguaaacg gccacaaguu uu                                              22

<210> SEQ ID NO 22
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 22
acuuguggcc guuuacgucg cu                                              22

<210> SEQ ID NO 23
<211> LENGTH: 10
<212> TYPE: DNA
<213> ORGANISM: Artificial sequence
<220> FEATURE:
<223> OTHER INFORMATION: Synthetic oligonucleotide

<400> SEQUENCE: 23
gacgtaaacg                                                            10

<210> SEQ ID NO 24
<211> LENGTH: 12
<212> TYPE: DNA
<213> ORGANISM: Artificial sequence
<220> FEATURE:
<223> OTHER INFORMATION: Synthetic oligonucleotide
```

```
<400> SEQUENCE: 24
gccacaagut cu                                                    12

<210> SEQ ID NO 25
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 25
gacguaaacg gccacaag                                              18
```

US 9,051,570 B2

UNA OLIGOMERS FOR THERAPEUTICS

SEQUENCE LISTING

This application includes a sequence listing submitted herewith via EFS as an ASCII file created on Oct. 15, 2012, named Sequence Listing from 08-07 PCT 5-21-08.txt, which is 5335 bytes in size, and is hereby incorporated by reference in its entirety.

BACKGROUND

RNA interference (RNAi) has attracted massive attention in recent years, as it provides a means to silence the expression of a target gene. It provides basic research with a method for studying genetic and biochemical pathways, and the function of individual genes and gene products. Consequently, RNA interference has become a critical tool for target validation in the pharmaceutical industry. Moreover, substantial investments have been made with the goal of developing RNA complexes capable of mediating RNA interference complexes that can be used as drugs.

The attractiveness of RNAi for use in therapy lies in its sensitivity and sequence specificity. However, concerns have arisen concerning sequence specificity, e.g. because the wrong strand of the RNA complex may direct the response to the wrong target nucleic acids. Moreover, RNA complexes of a certain size induce a non-specific interferon dependent response, which is also undesirable.

Patent application US2003/0108923 describes RNA complexes capable of mediating RNAi comprising an antisense strand and a passenger strand, wherein the strands are 21-23 nucleotides in length. It is suggested that the RNA complexes are used for therapeutic applications.

Similarly, patent application US2005/0234007 describes RNA complexes capable of mediating RNAi comprising an antisense strand and a passenger strand, wherein the complex comprises 3'-overhangs. It is suggested that the RNA complexes are used for therapeutic applications.

WO2005/073378 describes RNAi complexes containing chemically modified nucleotides capable of mediating RNAi comprising an antisense strand and a passenger strand. The RNA complexes described in the specification comprise LNA residues and it is stated that incorporation of LNA residues near the 5' end of one of the strand can control which strand is incorporated in the RISC complex, because the strand that forms the weakest base pair at its 5-end is incorporated into the RISC complex.

RNAi is only one of several strategies for mediating inhibition of gene expression using oligonucleotides, including the RNA complexes of this invention. These different strategies, that include RNase H mediated RNA cleavage, steric block RNA binding, DNAzyme or Ribozyme mediated RNA cleavage and siRNA approaches have been described in the literature together with the nature of selected chemically modified nucleotides that are compatible with biological activity [J. Kurreck, Eur. J. Biochem. 2003, 270, 1628].

The hydroxymethyl substituted monomers B-E of the invention have been incorporated into DNA strands, and therefore procedures for preparation of their phosphoramidite building blocks for automated DNA/RNA synthesis have been reported [K. D. Nielsen et al., Bioorg. Med. Chem. 1995, 3, 1493; H. Thrane et al., Tetrahedron 1995, 51, 10389; P. Nielsen et al., Bioorg. Med. Chem. 1995, 3, 19]. It is exclusively thymine monomers that have been incorporated into DNA strands. None of the hydroxymethyl substituted monomers have previously been incorporated into RNA strands.

In one report, one or two 2'-secouridines was incorporated into a DNA oligonucleotide and a positive effect on RNase H mediated RNA degradation was observed (Mangos M M, Min K L, Viazovkina E, Galarneau A, Elzagheid M I, Parniak M A, Damha M J., J Am Chem Soc. 2003 Jan. 22; 125 (3):654-61).

SUMMARY

The present invention provides RNA complexes with one or more hydroxymethyl substituted monomers incorporated into an RNA strand to be used in relation to RNA-guided gene regulation or gene analysis, in particular RNA interference. Thus, it is an object of the present invention to provide RNA complexes, which have reduced off target effects as compared to the RNA complexes typically used. Another object is to provide RNA complexes which induce a reduced interferon response. Still another object is to provide RNA complexes with improved properties with regard to stability towards enzymatic degradation in cell cultures or in vivo. Still another object is to provide RNA complexes that display enhanced gene regulatory function, e.g. gene silencing effect, in cell cultures or in vivo, relative to the unmodified RNA complexes. Yet further objects are to provide RNA complexes that are targeted towards specific organs or tissue, and that are capable of penetrating the cell membrane. The present invention also provides monomers suitable for incorporation of hydroxymethyl substituted monomers into oligonucleotides and methods for their synthesis.

BRIEF DESCRIPTION OF DRAWINGS

FIG. 1

Figure 3:
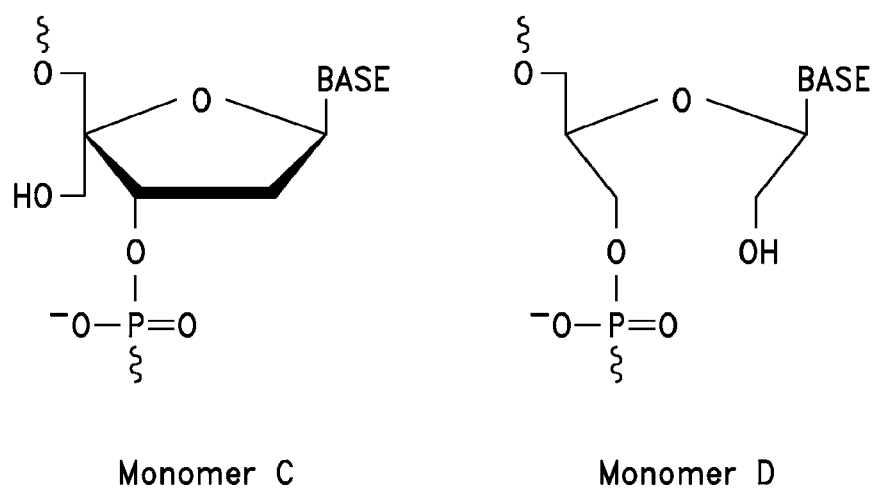

Examples of the different architectures of the hydroxymethyl substituted nucleotides that are incorporated in the RNA complexes are shown. Monomer A is shown for comparison and is a natural RNA monomer with its ribose scaffold. The characteristic of Monomers B-E that are comprised in the RNA complexes of the invention is that they contain a substituent that is a hydroxymethyl group ("the free hydroxymethyl group"), and therefore the invention is entitled "Hydroxymethyl substituted RNA oligonucleotides and RNA complexes". The free hydroxymethyl group is for example attached at the C4' atom of a cyclic ribose scaffold or the C1' atom of an acyclic ribose-based scaffold. The hydroxymethyl substituted nucleotides of the invention contain other oxygen atoms that are each attached to a phosphorus atom and thus partake in the formation of internucleotide linkages (see FIG. 1). One or more of these other oxygen atoms can be part of a hydroxy group which is the case when one or more of the hydroxymethyl substituted nucleotides of the RNA complexes of the invention is (are) positioned at the 3'- or 5'-end of an RNA strand. When one of the hydroxymethyl substituted nucleotides of the RNA complexes of the invention is positioned at the 3'-end and/or the 5'-end of the RNA strands, a hydroxyl group of this monomer can be phosphorylated, as can be the case for any terminally positioned natural RNA monomer. To the hydroxymethyl substituted nucleotides of the invention is attached a nucleobase like uracil, thymine, cytosine, 5-methylcytosine, adenine, guanine or any other known natural or synthetic nucleobase or nucleobase analogue (designated as "Base" in FIG. 1).

FIG. 2

Derivatised, functionalised and conjugated variants of the hydroxymethyl substituted monomers are shown. As examples are shown derivatised, functionalised and conjugated variants of the hydroxymethyl substituted 2',3'-seco- RNA monomer D (see FIG. 1). Monomer F contains a group R linked via an ether linkage. Monomer G contains a group R linked via a thioether linkage. Monomer H contains a group R linked via an amide linkage. Monomer I contains a group R linked via an amino linkage. Monomer J contains a group R linked via a piperazino unit. By incorporation of one or several of such monomers into the RNA complexes of the invention, the properties of the RNA complexes can be modulated. For example can increased biostability, increased RNA targeting capability or specific delivery properties be introduced, and fluorescent groups can be attached for detection purposes.

FIG. 3

Structures of two of the hydroxymethyl substituted monomers (Monomer C and Monomer D) that may be a monomer of an oligonucleotide or RNA complex.

FIG. 4

Gene silencing results for siRNA complexes of the invention containing "monomer X" (i.e., 2',3'-seco-RNA Monomer D). Results were obtained with the W130 sense strand (see FIG. 4 for nucleotide sequence) containing Monomer D having uracil as the nucleobase (shown as 'X' in the W130 sense strand). The nucleic acid sequence of the antisense strands used in this study are listed at the bottom of this figure (all X monomers in the antisense sequences are Monomer D having uracil as the nucleobase). Monomers with a superscript "L" represent a locked nucleic acid (e.g., $T^L$ indicates a thymine locked nucleic acid or LNA).

FIG. 5

Gene silencing results for siRNA complexes of the invention containing "monomer X" (i.e., 2',3'-seco-RNA Monomer D). Results were obtained with the W131 sense strand (see FIG. 5 for nucleotide sequence) containing Monomer D having uracil as the nucleobase (shown as 'X' in the W131 sense strand). The nucleic acid sequence of the antisense strands used in this study are listed at the bottom of FIG. 4 (all X monomers in the antisense sequences are Monomer D having uracil as the nucleobase).

FIG. 6

Gene silencing results for siRNA complexes of the invention containing "monomer X" (i.e., 2',3'-seco-RNA Monomer D). These results were obtained with the W282 sense strand (see FIG. 6 for nucleotide sequence) containing Monomer D having as nucleobase cytosine (sC, first X from the 5'-end of the W282 sequence), adenine (sA, second X from the 5'-end of the W282 sequence) and cytosine (sC, last X from the 3'-end of the W282 sequence). The nucleic acid sequence of the antisense strands used in this study are listed at the bottom of FIG. 4 (all X monomers in the antisense sequences are Monomer D having uracil as the nucleobase).

FIG. 7

Gene silencing results for siRNA complexes of the invention containing "monomer X" (i.e., 2',3'-seco-RNA Monomer D). These results were obtained with the W194 sense strand (see FIG. 7 for nucleotide sequence). The nucleic acid sequence of the antisense strands used in this study are listed at the bottom of FIG. 4 (all X monomers in the antisense sequences are Monomer D having uracil as the nucleobase). Monomers with a superscript "L" represent a locked nucleic acid (e.g., $T^L$ indicates a thymine locked nucleic acid or LNA).

FIG. 8

Gene silencing results for siRNA complexes of the invention containing "monomer X" (i.e., 2',3'-seco-RNA Monomer D). These results were obtained with the W181 sense strand (see FIG. 8 for nucleotide sequence). The nucleic acid sequence of the antisense strands used in this study are listed at the bottom of FIG. 4 (all X monomers in the antisense sequences are Monomer D having uracil as the nucleobase). Monomers with a superscript "L" represent a locked nucleic acid (e.g., $T^L$ indicates a thymine locked nucleic acid or LNA).

FIG. 9

Gene silencing results for siRNA complexes of the invention containing "monomer X" (i.e., 2',3'-seco-RNA Monomer D). These results were obtained with the W129 sense strand (see FIG. 9 for nucleotide sequence) containing Monomer D having uracil as the nucleobase (shown as 'X' in the W129 sense strand). The antisense strands included in this study are listed at the bottom of FIG. 4 (all X monomers in the antisense sequences are Monomer D having uracil as the nucleobase). Monomers with a superscript "L" represent a locked nucleic acid (e.g., $T^L$ indicates a thymine locked nucleic acid or LNA).

DETAILED DESCRIPTION

Specific features described in one aspect of the invention also apply to other aspects of the invention. E.g. features described with regards to the RNA complexes of the first aspect also apply to the oligonucleotides of the ninth aspect and to the RNA duplexes of the tenth aspect where appropriate.

First Aspect, RNA Complexes

RNA complexes in the form of siRNA duplexes or single stranded RNA can mediate various modifications of target nucleic acids in the cell. In this process, the antisense strand of the complex acts as a guide, as the antisense strand can hybridise to target nucleic acids that have stretches of sequence complementarity to the antisense strand.

Before targeting of a target nucleic acid, the antisense strand is often incorporated into an RNA guided protein complex (RGPC), which can act upon the target nucleic acid. One example of a RNA guided protein complex is the RNA Induced Silencing Complex (RISC). It is believed that other such RGPCs exist and that the RNA complexes of the present invention will also be of advantage, when used with these other RGPCs or even without interacting with any RGPCs.

One object of the present invention is to stabilise the RNA complexes towards nucleolytic degradation in biological media (serum, in vivo, in cell cultures).

Another object of the present invention is to improve the gene silencing effect of a double stranded RNA complex. This improvement can, e.g. relate to increased potency, reduced off-target effects, reduced immune stimulation, increased stability for storage, increased stability in biological media like serum etc., increased duration of action and improved pharmacokinetic properties, all relative to the native unmodified RNA complex.

Yet another object of the present invention is to improve the gene silencing effect of a single stranded RNA oligonucleotide. This improvement can, e.g., relate to increased potency, reduced off-target effects, reduced immune stimulation, increased stability for storage, increased stability in biological media like serum etc., increased duration of action and improved pharmacokinetic properties, all relative to the native unmodified RNA complex.

It is an object of the invention to secure that only the antisense strand, and not the passenger strand, of an siRNA complex of the invention will mediate modifications of target nucleic acids. The fulfilment of this object will provide RNA complexes with less off target effects.

Another object of the invention is to ensure sufficient stability of an RNA complex in biological media. Thus it is an object to provide RNA complexes that display enhanced gene regulatory function, e.g. gene silencing effect, in cell cultures or in vivo, relative to unmodified RNA complexes.

The basic idea of the invention is to incorporate one or more hydroxymethyl substituted monomers into an RNA complex of the invention. In case of siRNA this could lead to preferential incorporation of only one strand of the complex into RISC. Incorporation of one or more hydroxymethyl substituted monomers into one (or more) RNA strand(s) of an RNA complex will improve the life time of the RNA complex in biological media and in vivo, and thus will lead to improved biological activity, for example improved gene regulation activity.

An RNA strand of an RNA complex of the invention may comprise natural RNA nucleotides, RNA modifications known to be compatible with gene silencing activity [Nawrot and Sipa, Curr. Topics Med. Chem. 2006, 6, 913-925], and the hydroxymethyl substituted monomers (FIG. 1). Phosphordiester linkages may connect the individual monomers, but modified linkages like phosphorothioate linkages and other linkages known to a person skilled in the field [Nawrot and Sipa, Curr. Topics Med. Chem. 2006, 6, 913-925] may be used instead. The RNA complexes may comprise two strands that together constitute an siRNA duplex composed of an antisense strand (the antisense strand is also herein referred to as the guide strand) and a passenger strand (the passenger strand is also herein referred to as the sense strand), but a single stranded microRNA mimicking molecule is also considered herein as an RNA complex of the invention, as is a single stranded antisense molecule that for example is useful for targeting microRNAs.

In the embodiments of the invention, the RNA complex comprises one or more hydroxymethyl modified nucleotide monomer(s) (see FIG. 1). Hereunder as one such example is an acyclic nucleotide monomer, more preferably an acyclic monomer selected from the group consisting of monomers D-J. Thus, the embodiments described in the first aspect with regards to hydroxymethyl modified nucleotide monomers will apply for other embodiments relating to acyclic nucleotide monomers.

The use of hydroxymethyl modified nucleotide monomers may be favoured for several reasons. They may e.g. be used to increase gene silencing effect of the RNA complexes and the incorporation of one or more hydroxymethyl modified nucleotide monomer(s), for example towards the ends of the RNA complexes induce significant stability towards nucleolytic degradation. They may also be used to decrease the gene silencing effect of the passenger strand of an siRNA complex thus reducing the number of off-target effects.

In one preferred embodiment of the invention, the RNA complex comprising one or more hydroxymethyl modified nucleotide monomer(s) is a single stranded RNA construct.

In one preferred embodiment of the invention, the RNA complex comprising one or more hydroxymethyl modified nucleotide monomer(s) is a single stranded RNA construct that is able to inhibit gene expression by acting as a single stranded antisense molecule.

In one preferred embodiment of the invention, the RNA complex comprising one or more hydroxymethyl modified nucleotide monomer(s) is a single stranded RNA construct that functionally mimics a microRNA.

In one preferred embodiment of the invention, the RNA complex comprising one or more hydroxymethyl modified nucleotide monomer(s) is an siRNA construct.

Accordingly, in one embodiment, the antisense strand of an siRNA construct comprises one or more hydroxymethyl modified nucleotide monomer(s).

In another embodiment, the passenger strand of an siRNA construct comprises one or more hydroxymethyl modified nucleotide monomer(s). In yet another embodiment, a first and second RNA molecule of a nicked passenger strand of an siRNA construct each contain one or more hydroxymethyl modified nucleotide monomer(s).

In one embodiment of the invention, the number of hydroxymethyl modified nucleotide monomers in the antisense strand is 10. In other embodiments of the invention, the number of hydroxymethyl modified nucleotide monomer(s) in the antisense strand is 9, 8, 7, 6, 5, 4, 3, 2 or 1, respectively.

In another embodiment, all nucleotides of the antisense strand are hydroxymethyl modified nucleotide monomers.

In a preferred embodiment, all hydroxymethyl modified nucleotide monomers in the antisense strand is present in positions 1-8, wherein the positions are counted from the 5'end. Even more preferably, the hydroxymethyl modified nucleotide monomers in the antisense strand is present in positions 2-7 corresponding to the so-called seed region of a microRNA. Thus, presence of hydroxymethyl modified nucleotide monomers in the aforementioned regions will prevent the antisense strand from acting as a microRNA, which reduces off target effects when the antisense strand is intended to function as siRNA.

In a preferred embodiment, at least one hydroxymethyl modified nucleotide monomer is present in one of positions 9-16, wherein the positions are counted from the 5'end. Even more preferred is the presence of 2, 3, 4, 5 or 6 hydroxymethyl modified nucleotide monomer is present in positions 9-16 and in another embodiment, hydroxymethyl modified nucleotide monomers in the antisense strand is present in all of positions 9-16. In one embodiment, hydroxymethyl modified nucleotide monomer are only present in regions 9-16 and not in the rest of the antisense strand.

Even more preferably, the hydroxymethyl modified nucleotide monomers in the antisense strand is present in position 9-11 and preferably, not in the rest of the oligonucleotide. The presence of hydroxymethyl modified nucleotide monomers in the aforementioned regions will induce the antisense strand to act as a microRNA, i.e. ensure that the siRNA effect will be minimal and the microRNA effect much higher. This effect likely stems from the reduced tendency towards full length binding because of reduced affinity caused by the presence of an acyclic hydroxymethyl substituted monomer, e.g. monomer D.

Likewise, in another embodiment of the invention, the number of hydroxymethyl modified nucleotide monomers in the passenger strand of an siRNA complex of the invention is 10. In other embodiments of the invention, the number of hydroxymethyl modified nucleotide monomers in the passenger strand of an siRNA complex of the invention is 9, 8, 7, 6, 5, 4, 3, 2 or 1, respectively.

In another embodiment, all nucleotides of the passenger strand of an siRNA complex of the invention are hydroxymethyl modified nucleotide monomers.

In one embodiment, both the antisense strand and the passenger strand of an siRNA complex of the invention contain one or more hydroxymethyl modified nucleotide monomer(s).

In one aspect, the present invention provides an RNA complex capable of mediating nucleic acid modifications of a target nucleic acid. Such RNA complex may e.g. be a siRNA, microRNA or microRNA precursor (pre-microRNA).

The RNA complex of an siRNA complex of the invention comprises a core double stranded region comprising an antisense strand and a passenger strand that is hybridised to the antisense strand.

A target nucleic acid as referred to in the present context is a nucleic acid, which has significant complementarity to the antisense strand of the complex. Preferably, complementarity is perfect over a stretch of several nucleotides.

Thus, in one embodiment, complementarity is perfect over a stretch of 25 nucleotides.

In other embodiments, complementarity is perfect over a stretch of 24 nucleotides, 23 nucleotides, 22 nucleotides, 21 nucleotides, 20 nucleotides, 19 nucleotides, 18 nucleotides, 17 nucleotides, 16 nucleotides, 15 nucleotides, 14 nucleotides, 13 nucleotides, 12 nucleotides, 11 nucleotides, 10 nucleotides, 9 nucleotides, 8 nucleotides, 7 nucleotides or 6 nucleotides, respectively.

In one embodiment, the stretch of complementarity comprises 1 mismatch. In other embodiments, the stretch of complementarity comprises 2 mismatches, 3 mismatches or 4 mismatches, respectively. A mismatch of 1 is a region in the stretch of complementarity where a base pair cannot form, e.g. when G is opposite to A. When more mismatches are present they may be adjacent to each other or they may be spaced in different regions of the stretch of complementarity.

The RNA complex of an siRNA complex of the invention comprises in a preferred embodiment a core double-stranded region, which is a substantially double-stranded region. Single-stranded regions in the RNA complex are primarily related to overhangs of the complex.

Thus, in one embodiment, the double-stranded region of an siRNA complex of the invention comprises 1 mismatch. In other embodiments, the double-stranded region comprises 2 mismatches, 3 mismatches and 4 mismatches, respectively.

As used herein, the term "target nucleic acid" encompasses any RNA/DNA that would be subject to modulation guided by the antisense strand, such as targeted cleavage or steric blockage. The target RNA/DNA could, for example be genomic DNA, genomic viral RNA, mRNA, a pre-mRNA, or a non-coding RNA As used herein, the term "target nucleic acid modification" means any modification to a target nucleic acid, including those that affect the activity of the target nucleic acid, without affecting the structure of the target nucleic acid.

A preferred target nucleic acid of the invention is mRNA. Accordingly, in one embodiment the nucleic acid modification mediated by the RNA complex is RNA interference (RNAi). In a preferred embodiment, RNAi mediates degradation of the mRNA. In another preferred embodiment, RNAi mediates translational inhibition of the mRNA. In another embodiment, the RNAi mediates both translational inhibition and degradation of the mRNA.

In other preferred embodiments, the target nucleic acid is a non-coding RNA, e.g. a tRNA, miRNA, snRNA, snoRNA or an rRNA.

In still another embodiment, the target nucleic acid is genomic DNA. In such embodiments, preferred nucleic acid modifications include DNA methylation and DNA deletion.

The size of the RNA complex of the invention can be varied while still fulfilling one or more objects of the invention. This e.g. applies where the particular object is reduced off-target effect.

Thus, the core double-stranded region of an siRNA complex of the invention may comprise a number of base pairs selected from the group of 10 base pairs, 11 base pairs, 12 base pairs, 13 base pairs, 14 base pairs, 15 base pairs, 16 base pairs, 17 base pairs, 18 base pairs, 19 base pairs, 20 base pairs, 21 base pairs, 22 base pairs, 23 base pairs, 24 base pairs and 25 base pairs, 26 base pairs, 27 base pairs, 28 base pairs, 29 base pairs, 30 base pairs, 35 base pairs, 40 base pairs, 42 base pairs, 45 base pairs, 50 base pairs, 55 base pairs, 60 base pairs or 62 base pairs.

In one embodiment, the core double stranded region of an siRNA complex of the invention comprises from 15 to 40 base pairs.

In another preferred embodiment, the core double stranded region of an siRNA complex of the invention comprises 18-22 base pairs.

In one embodiment, the core double stranded region of an siRNA complex of the invention is even longer than 40 base pairs, although it is known that in some cells, the introduction of longer double stranded RNA complex may induce an interferon dependent non-specific response. In one such embodiment, it is contemplated that the complex is processed to shorter double-stranded RNA complexes before engaging with a RGPC. An RNase III like enzyme such as DICER may execute processing. Dicer also processes double stranded RNA shorter than 40 base pairs and such RNA complexes (referred to as Dicer substrates) have various advantages as compared to siRNA that enters RISC without processing. Hence, in one embodiment, the RNA complexes of the invention are Dicer substrates.

In another embodiment, the RNA complex is single stranded and has no double stranded region.

In yet another embodiment, the RNA complex is single stranded but folds such that it contains one or more double stranded regions. Such embodiments are useful e.g. for mimicking microRNAs and their functions.

In yet another embodiment, the core double stranded region of an siRNA complex of the invention is shorter than 10 base pairs and thus comprises from one to nine base pairs.

In one embodiment of the invention, the core double stranded region of the RNA complex is comprised by more than two RNA strands.

In one embodiment of the invention, the core double stranded region of the RNA complex is comprised by three RNA strands.

In another embodiment of the invention, the core double stranded region of the RNA complex is comprised by four or more RNA strands.

In a preferred embodiment of the invention, the siRNA complex of the invention comprises overhangs. An overhang as used in the present context refers to a short single-stranded region following a double-stranded region.

In one embodiment, the antisense strand of an siRNA complex of the invention comprises a 3'-overhang.

In another embodiment, the passenger strand of an siRNA complex of the invention comprises a 3'-overhang.

In yet another embodiment, the antisense strand of an siRNA complex of the invention comprises a 5'-overhang.

In still another embodiment, the passenger strand of an siRNA complex of the invention comprises a 5'-overhang.

In a preferred embodiment, both the antisense strand and the passenger strand of an siRNA complex of the invention comprise a 3'-overhang.

The overhangs of an siRNA complex of the invention can be of varying length, without interfering with the basic function of the complex. Thus, in one embodiment the overhangs are selected from the group of overhangs with a length of 1 nucleotide, 2 nucleotides, 3 nucleotides, 4 nucleotides, 5 nucleotides, 6 nucleotides, 7 nucleotides and 8 nucleotides.

Most preferred overhangs of an siRNA complex of the invention are overhangs with a length of 1, 2 and 3 nucleotides, respectively.

In one embodiment, the overhang of the antisense strand of an siRNA complex of the invention has the same length as the overhang of the passenger strand.

In another embodiment, the overhang of the antisense strand of an siRNA complex of the invention does not have the same length as the overhang of the passenger strand In still another embodiment of an siRNA complex of the invention, the RNA complex comprises at least one blunt end. A "blunt end" refers to an end of a double-stranded nucleic acid, which does not have any protruding nucleotides, i.e. both strands of the double-stranded nucleic acid ends at the same position.

In another embodiment, the siRNA complex of the invention is blunt ended at both ends.

Preferred RNA complexes of the invention are similar in overall structure to the products of DICER processing of longer double stranded RNA complexes. In another embodiment, the RNA complexes of the invention are Dicer substrates as mentioned above.

Other preferred RNA complexes of the invention are complexes wherein the core double-stranded region comprises 18-22 base pairs, and wherein the antisense strand and the passenger strand each comprise a 3'-overhang of 1-3 nucleotides.

The antisense strand of the RNA complex of the invention can have varying lengths, without interfering with the function of the complex. Thus, in preferred embodiments, the antisense strand is an 8-mer, 9-mer, 10-mer, 11-mer, 12-mer, 13-mer, 14-mer, 15-mer, 16-mer, 17-mer, 18-mer, 19-mer, 20-mer, 21-mer, 22-mer, 23-mer, a 24-mer, a 25-mer, a 26-mer, a 27-mer, a 28-mer, 29-mer, 30-mer, 31-mer, 32-mer, 33-mer, 34-mer, 35-mer, 36-mer, 37-mer, 38-mer, 39-mer, 40-mer, 41-mer, 42-mer, 43-mer, 44-mer, 45-mer, 46-mer, 47-mer, 48-mer, 49-mer, 50-mer, 51-mer, 52-mer, 53-mer, 54-mer, 55-mer, 56-mer, 57-mer, 58-mer, 59-mer, 60-mer, 61-mer or a 62-mer, respectively. It is to be understood that e.g. a 19-mer is an antisense strand of 19 monomers, i.e. 19 nucleotides.

In another preferred embodiment, the antisense strand of the RNA complex is selected from the following group of antisense strands: A 15-mer, 16-mer, 17-mer, 18-mer, 19-mer, 20-mer, 21-mer, 22-mer and a 23-mer. In one embodiment the passenger strand of an siRNA complex of the invention is discontinuous. In one embodiment of an siRNA complex of the invention, the passenger strand comprises several separate RNA molecules. The number of RNA molecules may be 1, 2, 3, 4, 5 or 6.

In one embodiment, the length of individual RNA molecules of the passenger strand of an siRNA complex of the invention is above 4 monomers. In other embodiments, the length of individual RNA molecules of the passenger strand is above 5 monomers, 6 monomers, 7 monomers, 8 monomers, 9 monomers, 10 monomers, 11 monomers and 12 monomers, respectively.

In other embodiments, the length of individual RNA molecules of the passenger strand of an siRNA complex of the invention is below 5 monomers, 6 monomers, 7 monomers, 8 monomers, 9 monomers, 10 monomers, 11 monomers and 12 monomers, respectively.

In one embodiment of the invention, a discontinuous passenger strand of an siRNA complex of the invention comprises a first and a second RNA-molecule, which together forms the discontinuous passenger strand, wherein the first RNA molecule is hybridised to the downstream part of the antisense strand and the second RNA molecule is hybridised to the upstream part of the antisense strand.

In one embodiment, the antisense strand of an siRNA complex of the invention is discontinuous. Preferred discontinuities of the antisense strands are the same as the preferred discontinuities of the passenger strand.

A discontinuity of one of the strands of an siRNA complex of the invention can be a nick. A nick is to be understood as a discontinuity in one strand of a double-stranded nucleic acid caused by a missing phosphodiester bond, however, without the double-stranded nucleic acid missing a nucleotide. Thus, the bases opposite to the nick will still be hybridised to bases on the nicked strand.

Another discontinuity of one of the strands of an siRNA complex of the invention is an alternative nick, which is understood as a discontinuity in one strand of a double-stranded nucleic acid caused by one missing bond, or more than one missing bond in the sugar-phosphate backbone, other than a phosphodiester bond, however, without the double-stranded nucleic acid missing a nucleobase. Thus, the bases opposite to the nick may still be hybridised to bases on the nicked strand.

A gap as used as a nomination when an RNA strand of an RNA complex of the invention can be described to have a discontinuity where at least one nucleotide or nucleoside or a nucleobase is missing in the double-stranded nucleic acid.

Preferably, the 5'-ends of the RNA complex is phosphorylated or is available for phosphorylation. Available for phosphorylation means that the 5'-hydroxy group has not been blocked e.g. by direct conjugation or by other conjugation to other groups in the vicinity of the 5'-hydroxy group, which will prevent the 5'-hydroxy group from being phosphorylated.

Hence, in a preferred embodiment of the invention, the RNA molecule(s) of the RNA complex comprise(s) a 5'-end phosphate and a 3'-hydroxy group.

In another embodiment, the second RNA molecule of an siRNA complex of the invention comprises a 5'-end phosphate and a 3'-hydroxy group.

In yet another embodiment, the antisense strand comprises a 5'-end phosphate and a 3'-hydroxy group.

In some embodiments of the invention, it is preferred that the RNA complex comprises nucleotide analogues other than the hydroxymethyl modified nucleotides. Such nucleotide analogues other than the hydroxymethyl modified nucleotides are termed below as "alternatively modified nucleotides".

The use of alternatively modified nucleotides may be favoured for several reasons. They may e.g. be used to increase the melting temperature of the core double stranded region of an siRNA complex of the invention.

The use of alternatively modified nucleotides may be favoured to increase the melting temperature of the double stranded structure formed between the antisense strand and the target nucleic acid.

Accordingly, in one embodiment, the antisense strand comprises alternatively modified nucleotides.

In another embodiment, the passenger strand of an siRNA complex of the invention comprises alternatively modified nucleotides.

In yet another embodiment, a first and second RNA molecule of the passenger strand of an siRNA complex of the invention each contain alternatively modified nucleotides.

In one embodiment of the invention, the number of alternatively modified nucleotides in the RNA complex is 10. In other embodiments of the invention, the number of nucleotide analogues in the RNA complex is 9, 8, 7, 6, 5, 4, 3, 2 or 1, respectively.

In one embodiment of the invention, the number of alternatively modified nucleotides in the antisense strand is 10. In other embodiments of the invention, the number of nucleotide analogues in the antisense strand is 9, 8, 7, 6, 5, 4, 3, 2 or 1, respectively.

In another embodiment, all nucleotides of the antisense strand are alternatively modified nucleotides or a combination of alternatively modified nucleotides and hydroxymethyl-substituted nucleotides.

Likewise, in another embodiment of the invention, the number of nucleotide analogues in the passenger strand of an siRNA complex of the invention is 10. In other embodiments of the invention, the number of nucleotide analogues in the passenger strand is 9, 8, 7, 6, 5, 4, 3, 2 or 1, respectively.

In another embodiment, all nucleotides of the passenger strand of an siRNA complex of the invention are nucleotide analogues or a combination of alternatively modified nucleotides and hydroxymethyl-substituted nucleotides.

In one embodiment, both the antisense strand and the passenger strand of an siRNA complex of the invention contain alternatively modified nucleotides.

In one embodiment, the alternatively modified nucleotides of the RNA complex are identical, i.e. they are for example all LNA or all 2'-O-Me-RNA. In another embodiment, various different alternatively modified nucleotides are used in the same RNA complex.

In one embodiment, the RNA complex comprises phosphorothioate linkages.

In another embodiment, the RNA complex comprises a mixture of natural phosphordiester and phosphorothioate linkages.

Preferred nucleotide analogues of the invention is nucleotide analogues selected from the group of 2'-O-alkyl-RNA monomers, 2'-amino-DNA monomers, 2'-fluoro-DNA monomers, LNA monomers, HNA monomers, ANA monomers, FANA monomer, DNA monomers, PNA monomers and INA monomers, but other monomers can also be used [Nawrot and Sipa, *Curr. Topics Med. Chem.* 2006, 6, 913-925].

In one embodiment the hydroxymethyl substituent of the hydroxymethyl substituted monomers of the invention is functionalised by a conjugating group. A conjugating group is a group known to a Person skilled in the art that changes, expands or improves the properties of an RNA complex of the invention. Such groups may be useful for modulating cellular distribution, organ distribution, tissue distribution, duplex melting temperatures, target affinity, biostability, signalling of hybridization etc.

In one embodiment the hydroxymethyl substituent of the hydroxymethyl substituted monomers of the invention is functionalised by an ether linkage between a conjugated group and the methylene group of the hydroxymethyl substituent. See FIG. 2 (Monomer F).

In one embodiment the hydroxymethyl substituent of the hydroxymethyl substituted monomers of the invention is converted into a thioether functionality before incorporation into the RNA complex of the invention using methods known to a Person skilled in the art. See FIG. 2 (Monomer G).

In another embodiment the hydroxymethyl substituent of the hydroxymethyl substituted monomers of the invention is converted into a mercaptomethyl functionality before incorporation into the RNA complex of the invention using methods known to a Person skilled in the art. See FIG. 2 (Monomer G, R=H). This mercapto functionality is properly protected as e.g. its acetyl derivative during RNA synthesis using methods know to a Person skilled in the art.

In one embodiment the hydroxymethyl substituent of the hydroxymethyl substituted monomers of the invention is converted into an amine functionality before incorporation into the RNA complex of the invention using methods known to a Person skilled in the art. See FIG. 2 (Monomer I, R=H). This amine functionality is properly protected as e.g. its trifluoroacetyl or Fmoc derivative during RNA synthesis using methods know to a Person skilled in the art.

In one embodiment the hydroxymethyl substituent of the hydroxymethyl substituted monomers of the invention is acting as a handle for attachment of amide-linked conjugating groups. This involves conversion of the hydroxyl unit of the hydroxymethyl substituent into an amine unit, for example as described above, and further derivatisation of this amino group by e.g. a conjugating group by amide bond formation using methods known to a Person skilled in the art. This may take place before RNA synthesis or after RNA synthesis using methods known to a Person skilled in the art (FIG. 2, Monomer H)

In one embodiment the hydroxymethyl substituent of the hydroxymethyl substituted monomers of the invention is acting as a handle for attachment of amino-linked conjugating groups. This involves conversion of the hydroxyl unit of the hydroxymethyl substituent into an amine unit, for example as described above, and further derivatisation of this amino group by e.g. a conjugating group by amine bond formation using methods known to a Person skilled in the art. This may take place before RNA synthesis or after RNA synthesis using methods known to a Person skilled in the art (FIG. 2, Monomer I).

In still one embodiment, the amine group used for conjugation is an amino group, a piperazino group or a diamino alkyl group. Such monomers are called amine-derivatised monomers. Each of these groups may be further derivatised or conjugated (FIG. 2, Monomer J).

In one embodiment, the RNA complex of the invention has reduced off target effects as compared to native RNA complexes.

In one preferred embodiment, the RNA complex has at least one hydroxymethyl-substituted monomer of the invention in the antisense strand.

In another preferred embodiment, the RNA complex has at least one hydroxymethyl-substituted monomer of the invention incorporated in or around the so-called seed region of the antisense strand, i.e. in at least one of positions no. 1-12 from the 5'-end of the antisense strand.

In yet another preferred embodiment, the RNA complex has at least one hydroxymethyl-substituted monomer of the invention incorporated in at least one of positions no. 2-10 from the 5'-end of the antisense strand.

In yet another preferred embodiment, the RNA complex has one hydroxymethyl-substituted monomer of the invention incorporated in one of positions no. 3-8 from the 5'-end of the antisense strand.

In yet another preferred embodiment, the RNA complex has one hydroxymethyl-substituted monomer of the invention incorporated in one of positions no. 7 or 8 from the 5'-end of the antisense strand.

In yet another preferred embodiment, the RNA complex has one hydroxymethyl-substituted monomer of the invention incorporated in position no. 7 from the 5'-end of the antisense strand.

In yet another preferred embodiment, the RNA complex has one hydroxymethyl-substituted monomer of the invention incorporated in positions no. 9-16 from the 5'-end of the antisense strand.

In yet another preferred embodiment, the RNA complex has one hydroxymethyl-substituted monomer of the invention incorporated in positions no. 9-11 from the 5'-end of the antisense strand.

In yet another preferred embodiment, the RNA complex has one hydroxymethyl-substituted monomer of the invention incorporated in positions no. 9-10 from the '-end of the antisense strand.

In another embodiment, the RNA complex of the invention produces a reduced immune response as compared to native RNA complexes.

In still another embodiment, the RNA complexes of the invention have a prolonged effect as compared to native RNA complexes.

In yet another embodiment, the RNA complexes of the invention have an increased effect as compared to native RNA complexes. Accordingly, in a preferred embodiment, the RNA complex mediate RNAi more effectively than the native RNA complex, e.g. by more efficient degradation of target mRNA or by more efficient translational inhibition of target mRNA.

In still another embodiment, the RNA complexes of the invention are delivered efficiently to specific organs or tissues of a human or an animal.

In yet still another embodiment, the RNA complexes of the invention are able to penetrate the cell membrane efficiently.

In yet still another embodiment, the RNA complexes of the invention are able to penetrate the cell membrane more efficiently that natural RNA complexes.

In one embodiment, the RNA complexes of the invention are able to bind to plasma proteins which increases the retention of the RNA complexes in the human body.

Second Aspect, Preparation of RNA Complex

Another aspect of the invention is a method of preparing a two stranded RNA complex of the invention comprising incubating the antisense strand with the passenger strand under conditions wherein a RNA complex comprising a core double stranded region is formed, said RNA complex being capable of mediating RNA interference of a corresponding cellular RNA.

In alternative embodiments of this aspect, the RNA complex is substituted by an RNA duplex of the invention (tenth aspect).

Third Aspect, Method of Mediating Nucleic Acid Modification

Still another aspect of the invention is a method of mediating nucleic acid modification of a target nucleic acid in a cell or an organism comprising the steps:
  a. Contacting a cell or organism with the RNA complex of the invention under conditions wherein modification of a target nucleic acid can occur
  b. Thereby mediating modification of a target nucleic acid In preferred embodiments, the method of mediating nucleic acid modification of a target nucleic acid is performed in vitro.

In preferred embodiments, the method of mediating nucleic acid modification of a target nucleic acid is performed in vivo, i.e. in animals, in humans or in non-human animals.

In preferred embodiments, the method of mediating nucleic acid modification of a target nucleic acid is performed in cell cultures.

In yet another embodiment, the method is performed on an isolated cell.

In a preferred embodiment, the nucleic acid modification of the method is RNA interference, preferable degradation of target mRNA or translational inhibition of target mRNA or inhibition of other types of RNA, e.g. non-coding RNA.

In another embodiment, the nucleic acid modification is DNA methylation.

In alternative embodiments of this aspect, the RNA complex is substituted by either an oligonucleotide of the invention (ninth aspect) or an RNA duplex of the invention (tenth aspect).

Fourth Aspect, Method of Examining Gene Function

Another aspect of the invention is a method of examining the function of a gene in a cell or organism comprising:
  a. Introducing a RNA complex of the invention corresponding to said gene into the cell or organism, thereby producing a test cell or test organism
  b. Maintaining the test cell or test organism under conditions under which modification of a target nucleic acid can occur
  c. Observing the phenotype of the test cell or organism produced in step b and optionally comparing the observed phenotype with the phenotype of an appropriate control cell or control organism, thereby providing information about the function of the gene.

The RNA complex of the invention can be introduced into cells e.g. using transfection, as outlined in the appended examples.

The phenotype of the organism or cell may be observed e.g. using proteomics to assess protein levels or using microarrays to assess RNA levels. Also a more defined phenotype may be used, e.g. the expression of one particular gene.

The information obtained about the function of a gene may be used to determine whether a gene product is a suitable target for therapeutic intervention in relation to a particular disease. Thus, if it is demonstrated that a certain gene product act in a certain biochemical pathway known to be affected in e.g. a specific subtype of cancer, the gene product might be a suitable target for therapeutic intervention for treatment of the aforementioned subtype of cancer.

In a preferred embodiment of the method of examining the function of a gene in a cell or organism, the nucleic acid modifications of the method are RNA interference, preferable degradation of target mRNA or translational inhibition of target RNA.

In another embodiment, the nucleic acid modification is DNA methylation.

In preferred embodiments of the method of examining the function of a gene in a cell or organism, the method is performed in cell cultures, in vitro or in vivo.

In yet another embodiment, the method is performed on an isolated cell.

In alternative embodiments of this aspect, the RNA complex is substituted by either an oligonucleotide of the invention (ninth aspect) or an RNA duplex of the invention (tenth aspect).

Fifth Aspect, Method of Evaluating Agent

Another aspect of the invention is a method of assessing whether an agent acts on a gene product comprising the steps:
  a. Introducing the RNA complex of the invention corresponding to said gene into a cell or organism, thereby producing a test cell or test organism
  b. Maintaining the test cell or test organism under conditions under which modification of a target nucleic acid occurs
  c. Introducing the agent into the test cell or test organism
  d. Observing the phenotype of the test cell or organism produced in step c and optionally comparing the observed phenotype with the phenotype of an appropriate control cell or control organism, thereby providing information about whether the agent acts on the gene product A preferred control in step d is a test cell or test organism that has not had the RNA complex of step a introduced.

In a preferred embodiment of the method of assessing whether an agent acts on a gene or gene product, the nucleic acid modifications of the method are RNA interference, preferable degradation of target RNA or translational inhibition of target RNA. In another embodiment, modification of nucleic acid modifications is DNA methylation.

In preferred embodiments of the method of assessing whether an agent acts on a gene product, the method is performed in cell cultures, in vitro or in vivo.

In yet another embodiment, the method is performed on an isolated cell.

In alternative embodiments of this aspect, the RNA complex is substituted by either an oligonucleotide of the invention (ninth aspect) or an RNA duplex of the invention (tenth aspect).

Sixth Aspect, Pharmaceutical Composition

Still another aspect of the invention is the RNA complex and a pharmaceutically acceptable diluent, carrier or adjuvant. It will be apparent to the skilled man that the RNA complexes of the invention can be designed to target specific genes and gene products. It is to be understood that the RNA complexes will target a DNA sequence or a RNA sequence, and not a protein. However, the level of a gene product such as a protein may be affected indirectly, if its mRNA or a non-coding RNA is modified e.g. by RNA degradation or translational inhibition. Also the expression of the gene encoding the protein may be affected, e.g. because of DNA methylation.

In alternative embodiments of this aspect, the RNA complex is substituted by either an oligonucleotide of the invention (ninth aspect) or an RNA duplex of the invention (tenth aspect).

Seventh Aspect, Use a Medicament

Thus, another aspect is the RNA complex of the invention for use as a medicament. Once a therapeutic target has been validated, the skilled man can design RNA complexes that affect the level and the activity of the target, because the specificity of the RNA complexes lies exclusively within the sequence of the antisense strand. For native RNA complexes with a continuous passenger strand, there remains a problem with off-target effects due to the passenger strand acting as a guide sequence.

In alternative embodiments of this aspect, the RNA complex is substituted by either an oligonucleotide of the invention (ninth aspect) or an RNA duplex of the invention (tenth aspect).

Eighth Aspect, Monomers

An aspect of the invention is monomers suitable for incorporation of the hydroxymethyl substituted monomers of the invention and methods for their preparation from readily available starting materials. Thymin-1-yl derivatives of hydroxymethyl substituted monomers of the invention have been incorporated into DNA strands, and procedures for preparation of their phosphoramidite building blocks for automated DNA/RNA synthesis have been reported [K. D. Nielsen et al., *Bioorg. Med. Chem.* 1995, 3, 1493; H. Thrane et al., *Tetrahedron* 1995, 51, 10389; P. Nielsen et al., *Bioorg. Med. Chem.* 1995, 3, 19].

Most often, the RNA complexes of the invention will be prepared by automated oligonucleotide synthesis as known to a Person skilled in the art.

The incorporation of the hydroxymethyl substituted monomers of the invention into the RNA complexes of the invention follows standard methods for a) RNA synthesis on an automated RNA synthesizer, b) RNA work-up, c) RNA purification and d) RNA isolation [F. Eckstein, Oligonucleotides and Analogues, IRL Press, Oxford University Press, 1991]. The hydroxymethyl substituted RNA oligonucleotides (=RNA strands) and RNA complexes can be synthesised using phosphoramidite derivatives using the standard techniques for RNA synthesis.

In a preferred embodiment, methods of preparation of the phosphoramidite derivatives of the hydroxymethyl substituted monomers of the invention begins from a ribonucleoside, for example a O5'-DMT protected derivative of a ribonucleoside that for the bases adenine, guanine, cytosine and 5-methylcytosinecontains base protecting groups like for example, benzoyl, isobutyryl, acetyl, phenoxyacetyl, tert-butylphenoxyacetyl or other standard base protecting groups known to a Person skilled in the art.

In a preferred embodiment, the invention comprises methods to prepare monomeric building blocks suitable for incorporation of the Monomers D and E having a 2',3'-cleaved carbon-carbon bond (ribonucleoside nomenclature).

In other preferred embodiments, the invention comprises methods to prepare monomeric building blocks suitable for incorporation of the Monomers like F-J having a 2',3'-cleaved carbon-carbon bond and in addition carrying a functionality or group at for example its 2'-carbon atom (ribonucleoside nomenclature) other than a hydroxy group.

In a preferred embodiment of the invention, the method of preparation of the phosphoramidite derivatives of Monomer D comprises among the key steps 2',3'-glycol cleavage, reduction of the resulting intermediate, selective O2'-protection and O3'-phosphitylation.

In a preferred embodiment the 2',3'-glycol cleavage is undertaken using oxidative cleavage with for example sodium Periodate as reagent.

In another preferred embodiment the reduction of the intermediate after sodium Periodate cleavage is reduced to the corresponding diol effected by for example sodium borohydride.

For incorporation of Monomer D into the RNA complexes of the invention it is necessary to protect the 2'-hydroxy group (ribonucleoside nomenclature). In a preferred embodiment of the invention this is done by benzoylation. It may be beneficial to use only slightly more than one equivalent of benzoylation reagent (benzoyl chloride or e.g. benzoyl anhydride) in order to optimise the selectivity of the protection, i.e. the amount of O2'-benzoylation relative to O3'-benzoylation. In one preferred embodiment the benzoylation is performed below room temperature. In another useful embodiment the benzoylation is performed below 0° C. or even below −50° C.

In another preferred embodiment the O2'-protection is done by acetylation or by Performing acylation using an acylation reagent known to a Person skilled in the art of organic synthesis.

In another preferred embodiment the O2'-protection is done by silylation using a silylation reagent and method known to a Person skilled in the art of organic synthesis. A preferred silylation protecting group is tert-butyldimethylsilyl.

The subsequent phosphitylation reaction is in a preferred embodiment performed using either the so-called "PCl" reagent [PCl(OCH$_2$CH$_2$CN)(N(iPr)$_2$)] or the so-called "bis-amidite" reagent [P(OCH$_2$CH$_2$CN)(N(iPr)$_2$)$_2$].

In a preferred embodiment of the methods of preparation of the phosphoramidite derivatives of Monomer D, the starting material is a ribonucleoside, for example a O5'-DMT protected derivative of a ribonucleoside that for the bases adenine, guanine, cytosine and 5-methylcytosine contains base protecting groups like for example, benzoyl, isobutyryl, acetyl, phenoxyacetyl, tert-butylphenoxyacetyl or other standard base protecting groups known to a Person skilled in the art.

In another preferred embodiment, the invention provides a method of preparation of a phosphoramidite derivative of Monomer E.

In a preferred embodiment of the invention, the method of preparation of the phosphoramidite derivatives of Monomer E comprises among the key steps 2',3'-glycol cleavage, reduction of the resulting intermediate, selective O3'-protection and O2'-phosphitylation. The O3'-protection can for example be performed by silylation or acylation, or by a combination like first O2'-benzoylation, then O3'-silylation, and then O2'-debenzoylation. Other protecting groups may also be applied as would be clear for a Person skilled in the art.

In another preferred embodiments, the method to prepare monomeric building blocks suitable for incorporation of the Monomers like F-J, having a 2',3'-cleaved carbon-carbon bond and in addition carrying a functionality at its 2'-carbon atom (ribonucleoside nomenclature) other than a hydroxy group, comprises among the key steps starting from a ribonucleoside (for example a O5'-DMT protected ribonucleoside) 2',3'-glycol cleavage, reduction of the resulting intermediate, selective O3'-protection, conversion of the 2'-hydroxy group, O3'-deprotection and O3'-phosphitylation. The O3'-protection can for example be performed by silylation or acylation, or a combination of the both like first O2'-benzoylation, then O3'-silylation, and then O2'-debenzoylation. Other protecting groups may also be applied as would be clear for a person skilled in the art. The conversion of the 2'-hydroxy group into another group like amino, acylated amino, alkylated amino, dialkylated amino, carbamoylated amino, piperazino, acylated piperazino, alkylated piperazino, carbamoylated piperazino, mercapto, acylated mercapto, alkylated mercapto, disulfide, acylated hydroxy, alkylated hydroxy, carbamoylated hydroxy, etc., or by substituted and/or protected derivatives of these groups, can be performed using methods and procedures known to a person skilled in the art of organic synthesis. Such methods and procedures include substitution reactions on an activated derivative of the 2'-hydroxy group or acylation or carbamoylation reactions. Such methods and procedures also include O2'-alkylation reactions and alkylation reactions after inclusion of other C2' attached groups like amino or mercapto. Yet another possibility is oxidation of the 2'-hydroxy group to give an aldehyde functionality, which may be further modified by e.g. reaction with nucleophiles, or to give a carboxy functionality, which may be further modified by e.g. reaction with nucleophiles after conversion of the carboxy functionality into an antivated derivative like an active ester.

In another embodiment of the invention, the method to prepare monomeric building blocks suitable for incorporation of the Monomers like F-J, but "inversed" (like Monomers D and E can be considered "inversed") such that the O2' atom is phosphitylated and it is the 3'-hydroxy group that is converted into another group such that the C3' atom is linked to a functionality other that a hydroxy group, comprises among the key steps starting from a ribonucleoside (for example a O5'-DMT protected ribonucleoside) 2',3'-glycol cleavage, reduction of the resulting intermediate, selective O2'-protection, conversion of the 3'-hydroxy group, O2'-deprotection and O2'-phosphitylation. The O2'-protection can for example be performed by silylation or acylation, or a combination of the both. Other protecting groups may also be applied as would be clear for a person skilled in the art. The conversion of the 3'-hydroxy group into another group like amino, acylated amino, alkylated amino, dialkylated amino, carbamoylated amino, piperazino, acylated piperazino, alkylated piperazino, carbamoylated piperazino, mercapto, acylated mercapto, alkylated mercapto, disulfide, acylated hydroxy, alkylated hydroxy, carbamoylated hydroxy, etc., or by substituted and/or protected derivatives of these groups, can be performed using methods and procedures known to a person skilled in the art of organic synthesis. Such methods and procedures include substitution reactions on an activated derivative of the 3'-hydroxy group or acylation or carbamoylation reactions. Such methods and procedures also include O3'-alkylation reactions and alkylation reactions after inclusion of other C3' attached groups like amino or mercapto. Yet another possibility is oxidation of the 3'-hydroxy group to give an aldehyde functionality, which may be further modified by e.g. reaction with nucleophiles, or to give a carboxy functionality, which may be further modified by e.g. reaction with nucleophiles after conversion of the carboxy functionality into an antivated derivative like an active ester.

In one embodiment, a 2'-C-piperazino derivative is prepared by converting the 2'-hydroxy group into a leaving group (e.g. mesylate derivative) followed by reaction with a large excess of piperazine. This for example can be performed as a step toward synthesis of a phosphoramidite of structure Amidite J (see figure below).

In yet another embodiment, the invention comprises methods to prepare monomeric building blocks suitable for incorporation of the hydroxymethyl substituted monomers of the invention carrying groups or functionalities at the C1' atom (ribonucleoside nomenclature) that is different from a natural nucleobase. Such groups or functionalities, that may contain protecting groups, include e.g. pyrene, perylene, fluorophores, hydrogen, alkyl, reactive groups and heterocycles other than the natural nucleobases.

In yet another embodiment, the invention comprises methods to prepare monomeric building blocks suitable for incorporation of the hydroxymethyl substituted monomers of the invention that are constituted as H-phosphonate derivatives instead of phosphoramidite derivatives.

Below are shown examples of structures of some preferred embodiments of the invention with respect to phosphoramidite (=amidite) building blocks (DMT=4,4'-dimethoxytrityl; Base=natural nucleobase; CEtO=cyanoethoxy):

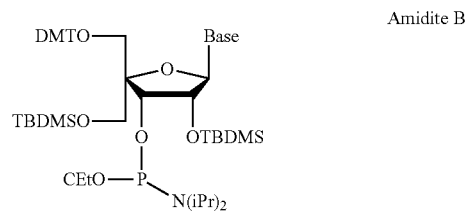

Amidite B

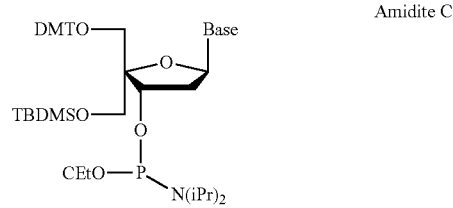

Amidite C

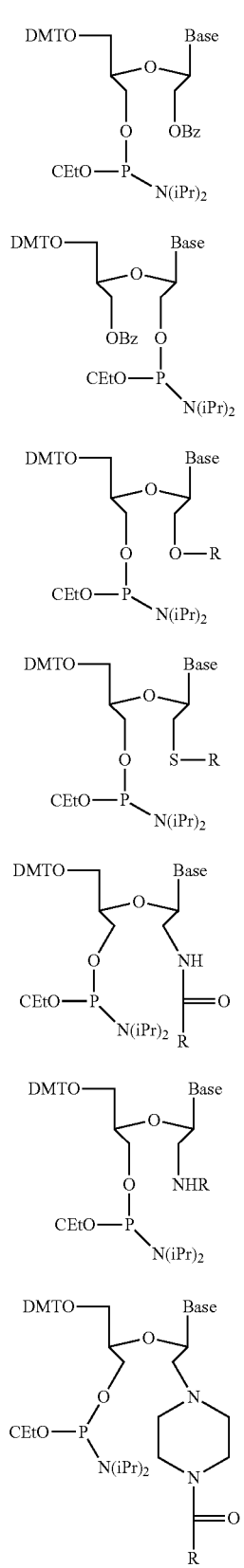

Amidite D

Amidite E

Amidite F

Amidite G

Amidite H

Amidite I

Amidite J

R = alkyl, cholesteryl derivatives, fluorophores, polyamines, fatty acids, amino acids, saccharides or polypeptides, etc.

Ninth Aspect, Oligonucleotide Comprising Acyclic Oligonucleotides

A ninth aspect of the invention is an oligonucleotide comprising an acyclic nucleotide monomer. As will be apparent from the description and the examples section such oligonucleotide has various uses and advantages.

In a preferred embodiment, the acyclic nucleotide monomer is a 2'-3'-seco-nucleotide monomer. Oligonucleotides of the invention comprising acyclic nucleotide monomers have surprisingly been found to be substrates cellular enzymes of the RNAi machinery and in some instances, these oligonucleotides are even better substrates than an identical oligonucleotide without acyclic nucleotide monomers.

Preferably, the acyclic nucleotide monomer is selected from the group consisting of monomer E, F, G, H, I or J (see FIG. 1). As will be clear to the skilled man, G, F, H, I and J can all be made from synthetic precursors of monomer D. As indicated in FIG. 2, the acyclic monomers may transformed into derivatives carrying conjugating groups such cholestoryl derivatives, alkyl, fluorophores, polyamines, amino acids, saccharides, polypeptides etc. Such conjugating groups may e.g. be useful for better biostability and/or biodistribution when the oligonucleotide is used for modulating the activity of target mRNAs in cells, organs or organisms.

The length of the oligonucleotide is preferably from 10 to 40 nucleotide monomers. Even more preferred is a length from 18 to 30 nucleotide monomers.

In a preferred embodiment, the oligonucleotide of the invention comprises less than 5 acyclic nucleotide monomers. In another preferred embodiment, the oligonucleotide comprises no more than 1 acyclic nucleotide monomer per 5 nucleotide monomers other than acyclic nucleotide monomers. Even more preferred is no more than 1 acyclic monomer per 8 nucleotide monomers other than acyclic nucleotide monomers. If the number of acyclic nucleotide monomer gets to high, the binding affinity of the oligonucleotide of the invention to a complementary nucleic acid is compromised.

Thus, in another embodiment, the oligonucleotide comprises from 1 to 5 acyclic nucleotide monomers.

In a preferred embodiment, acyclic nucleotide monomers are only present in one or more of position 1-8 and more preferably in positions 2-7 of the oligonucleotide. The positions are counted from the 5' end of the oligonucleotide. Acyclic nucleotide monomers in these regions will reduce or prevent the oligonucleotide from acting as a microRNA, as these positions correspond to the so-called seed region of a microRNA. This is relevant e.g. where the oligonucleotide is intended to function as the guide strand of an siRNA.

In a preferred embodiment, all hydroxymethyl modified nucleotide monomers in the antisense strand is present in positions 9-16, wherein the positions are counted from the 5' end. Even more preferably, the hydroxymethyl modified nucleotide monomers in the antisense strand is present in position 9-11. Thus, presence of hydroxymethyl modified nucleotide monomers in the aforementioned regions will induce the antisense strand to act as a microRNA, i.e. ensure that the siRNA effect will be minimal and the microRNA effect much higher. This effect likely stems from the reduced tendency towards full length binding because of reduced affinity caused by the presence of an acyclic hydroxymethyl substituted monomer, e.g. monomer D.

In a preferred embodiment, the oligonucleotide does not comprise DNA sequences of more than 8 consecutive DNA monomers. Even more preferred is no more than 6 consecutive DNA monomers and most preferably in no more than 4 consecutive DNA monomers. Consecutive DNA monomers typically will enable the oligonucleotide to activate RNase H when bound to a complementary RNA, which leads to degradation of the RNA. In some embodiments of the invention, this is not desirable. Thus, in a further embodiment, the oligonucleotide does not contain any DNA monomers at all.

In other embodiments, RNase H activation is desirable and it is preferred that the oligonucleotide comprises more than 4 consecutive DNA monomers, more preferably more 6 DNA monomers and most preferably more than 8 DNA monomers.

In yet another embodiment, the oligonucleotide comprises more than 50% RNA monomers. A high degree of RNA monomers will facilitate interaction with RNA-interacting proteins, e.g. by functioning as a substrate or guide (or co-factor) for a cellular enzyme such as RISC.

Thus, in another embodiment, it is preferred that more than 80% of the monomers of the oligonucleotide are RNA monomers. In yet another embodiment, it is preferred that more than 90% of the monomers of the oligonucleotide are RNA monomers.

As will be apparent, the oligonucleotide may also comprise nucleotide monomer analogues. In one such embodiment, acyclic nucleotide monomers and RNA monomers make up more than 80% of all nucleotide monomers. In another embodiment, acyclic monomers and RNA monomers make up more than 90% of all nucleotide monomers.

When the oligonucleotide comprises nucleotide monomer analogues, it is preferred that they are selected from the group consisting of 2'-O-alkyl-RNA monomers, 2'-amino-DNA monomers, 2'-fluoro-DNA monomers, LNA monomers, PNA monomers, HNA monomers, ANA monomers, FANA monomers, CeNA monomers, ENA monomers, DNA monomers and INA monomers. Nucleotide analogues are typically used to modulate binding affinity, increase biostability and in general give the oligonucleotide more drug-like properties.

In one embodiment, the oligonucleotide comprises at least 2 LNA nucleotide analogues. Acyclic nucleotide monomers typically decrease the melting temperature (i.e. binding affinity) of the oligonucleotide of the invention base paired to a complementary nucleic acid and LNA nucleotide monomers may be used to counteract this decrease in melting temperature. I.e. in one embodiment, the number of acyclic nucleotide monomers is identical to the number of LNA nucleotide monomers.

In a preferred embodiment, the oligonucleotide comprises only acyclic monomers and RNA monomers.

In another preferred embodiment, the oligonucleotide comprises only acyclic nucleotide monomers, RNA monomers, and LNA nucleotide analogues.

In a preferred embodiment, the oligonucleotide of the invention comprises one or more linkage(s) selected from the group consisting of phosphorothioate linkage, boranophosphate linkage, ethylphosphonate linkage, phosphoramidate linkage and phosphortriester linkage. Most preferred are a phosphorothioate linkage and/or a boranophosphate linkage. These linkages improve the biostability of the oligonucleotide and have also been shown to have a positive effect on the biodistribution of the oligonucleotide. In a preferred embodiment, the oligonucleotide comprises more than 50% of the aforementioned internucleotide linkages and even more preferably more than 75%. In one embodiment, all internucleotide linkages are of the aforementioned types.

In a preferred embodiment, the oligonucleotide of the invention is not base paired to a complementary oligonucleotide, i.e. the oligonucleotide of the invention is single stranded.

In yet another embodiment, the oligonucleotide is capable of mediating RISC dependent translational repression or degradation of target mRNAs complementary to the oligonucleotide. The skilled man will recognize RISC as the RNA Induced Silencing Complex and understand that in this embodiment, the oligonucleotide will act as a guide sequence for RISC and thereby guide RISC to RNA oligonucleotides, typically mRNAs that harbor partial or full complementarity to the oligonucleotide of the invention. When the oligonucleotide guides RISC to mRNA targets of partial complementarity, the oligonucleotide may be seen as a microRNA mimic and when the oligonucleotide guides RISC to mRNA targets of full complementarity; it may be seen as a single or double stranded siRNA.

RISC dependence may be assessed in cell lines by knocking out components of RISC using siRNA against the mRNAs encoding the RISC components and evaluate the activity of the oligonucleotide in the knock-out cell line. Such experiments are well known to those skilled in the art.

Tenth Aspect, RNA Duplex Comprising Oligonucleotide of Invention

A tenth aspect of the invention is an RNA duplex comprising a first oligonucleotide according to the invention and a second oligonucleotide.

In a preferred embodiment, the second oligonucleotide of the RNA duplex is also an oligonucleotide of the invention.

As will be clear, many of the features described with relation to the RNA complexes of the invention in the first aspect, are also applicable to RNA duplexes of the tenth aspect.

Preferably, the RNA duplex of the invention comprises a number of base pairs from 15 to 40 and in a preferred embodiment, comprises a number of base pairs selected from the group of 18 base pairs, 19 base pairs, 20 base pairs, 21 base pairs, 22 base pairs and 23 base pairs.

In yet another embodiment, the RNA duplex comprises a number of base pairs from 25 to 30, more preferably from 26 to 28 and most preferably 27 base pairs. Such RNA duplexes may be referred to as dicer substrate RNAs.

In a preferred embodiment, the RNA duplex of the invention comprises an overhang.

In another embodiment, the RNA duplex comprises two overhangs.

In still another embodiment, the first oligonucleotide comprises a 3'-overhang.

In still another embodiment, the second oligonucleotide comprises a 3'-overhang.

Preferably, the length of the overhang is from 1 to 8 nucleotides and even more preferably, the length of the overhang is selected from the group consisting of overhangs with a length of 1 nucleotide, 2 nucleotides and 3 nucleotides.

In another embodiment, the RNA duplex comprises at least one blunt end.

In another embodiment, the RNA duplex is blunt ended in both ends.

In a preferred embodiment, the RNA duplex comprises a double-stranded region of 18-22 base pairs, wherein the first oligonucleotide and the second oligonucleotide each comprise a 3'-overhang of 1-3 nucleotides. Such RNA duplex will be recognized as a canonical siRNA (short interfering RNA).

In one embodiment, one strand of the RNA duplex is discontinuous as described in detail in the first aspect.

In one embodiment, the RNA duplex is capable of mediating translational repression or degradation of target mRNA complementary to the first or the second oligonucleotide of the RNA duplex. I.e the RNA duplex will function as e.g. an siRNA, microRNA or pre-microRNA.

In one embodiment, the RNA duplex is capable of mediating translational repression or degradation of target mRNA while inducing reduced off-target effects as compared to an identical RNA duplex with RNA monomers instead of acyclic monomers. Reduced off targets may be achieved because of decreased binding affinity and also because either the first or the second oligonucleotide may be modified such as to not being able to function as a guide strand for RISC. I.e. it can be controlled which oligonucleotide of the RNA duplex function as passenger strand (sense strand) and which will function as guide strand (antisense strand).

In another embodiment, the RNA duplex is capable of mediating translational repression or degradation of target mRNA while inducing reduced off-target effects when specifically an acyclic monomer is positioned in position 5-10 in the guide (antisense) strand of an siRNA duplex, wherein the position is counted from the 5' end of the oligonucleotide.

In another embodiment, the RNA duplex is capable of mediating translational repression or degradation of target mRNA while inducing reduced off-target effects when specifically an acyclic monomer is positioned in position 6-8 in the guide (antisense) strand of an siRNA duplex. Not intended to be bound by theory, it is believed that the reduced binding affinity induced by the presence of the acyclic monomer at these positions that leads to reduced capability of the guide strand to induce microRNA-type effects. I.e. the acyclic monomer, when positioned correctly, reduces so-called seed-region binding, which is assumed to be more important for microRNA activity than for siRNA activity.

In one embodiment, the RNA duplex is capable of mediating RNA targeting, e.g. gene silencing or RNA interference, with increased potency as compared to an identical RNA duplex with RNA monomers instead of acyclic monomers. Increased potency may be achieved because of increased off-rate of the cleavage products of RISC reaction. The off-rate may be increased because of decreased binding affinity. Also increased flexibility of the substrate may increase the rate of hydrolysis. Furthermore the increased flexibility may ease unwinding of the RNA duplex prior to loading of the guide strand into RISC.

In one embodiment, the RNA duplex is capable of mediating translational repression or degradation of target mRNA with prolonged potency as compared to an identical RNA duplex with RNA monomers instead of acyclic monomers. Prolonged potency may for example be achieved because the oligonucleotides of the RNA duplex and the duplex per se are a poorer substrate for exo- and endonucleases and thereby the stability of the oligonucleotides and the duplex is increased.

In one embodiment, the RNA duplex is capable of mediating translational repression or degradation of target mRNA wherein the RNA duplex has improved biostability as compared to an identical RNA duplex with RNA monomers instead of acyclic monomers.

In yet another embodiment, the RNA duplex is capable of mediating translational repression or degradation of target mRNA wherein the RNA duplex has reduced immune stimulation as compared to an identical RNA duplex with RNA monomers instead of acyclic monomers. One reason for immune stimulation is interaction with Toll-like receptors that recognizes foreign oligonucleotides. Since RNA duplexes of the invention are non-natural, they will be more difficult to detect by the Toll-like receptors.

REFERENCES

US2003/0108923
US2005/0234007
WO2005/073378
J. Kurreck, *Eur. J. Biochem.* 2003, 270, 1628
K. D. Nielsen et al., *Bioorg. Med. Chem.* 1995, 3, 1493
H. Thrane et al., *Tetrahedron* 1995, 51, 10389
P. Nielsen et al., *Bioorg. Med. Chem.* 1995, 3, 19
Nawrot and Sipa, *Curr. Topics Med. Chem.* 2006, 6, 913-925
F. Eckstein, Oligonucleotides and Analogues, IRL Press, Oxford University Press, 1991
M. Petersen and J. Wengel, *Trends Biotechnol.* 2003, 21, 74-81
Pfundheller, Sørensen, Lomholt, Johansen, Koch and Wengel, J. "Locked Nucleic Acid Synthesis", *Methods Mol. Biol.* 2004, vol. 288 (Oligonucleotide Synthesis), 127-145, P. Herdewijn, Ed., Humana Press Inc.
Furniss, Hannaford, Smith and Tatchell, Vogel's Textbook of Organic Chemistry, 1989, John Wiley & Sons
Bryld, Højland and Wengel, *Chem. Commun.* 2004, 1064
Mokhir, Tetzlaff, Herzberger, Mosbacher and Richart, *J. Comb. Chem.* 2001, 3, 374
Mangos M M, Min K L, Viazovkina E, Galarneau A, Elzagheid M I, Parniak M A, Damha M J., *J Am Chem Soc.* 2003 Jan. 22; 125 (3):654-61

EXPERIMENTAL PROCEDURES AND EXAMPLES

Example 1

Synthesis of the RNA Complexes of the Invention

Procedures for preparation of the phosphoramidite building blocks for automated DNA/RNA synthesis of the hydroxymethyl substituted monomers of the RNA complexes of the invention have been reported [thymine derivatives; K. D. Nielsen et al., *Bioorg. Med. Chem.* 1995, 3, 1493; H. Thrane et al., *Tetrahedron* 1995, 51, 10389; P. Nielsen et al., *Bioorg. Med. Chem.* 1995, 3, 19]. Please see Example 11 for disclosure of procedures for preparation of example phosphoramidite derivatives of adenine, guanine, cytosine and uracil.

The incorporation of these hydroxymethyl substituted monomers into the RNA complexes of the invention follows standard methods for a) RNA synthesis on an automated RNA synthesizer, b) RNA work-up, c) RNA purification and d) RNA isolation [F. Eckstein, Oligonucleotides and Analogues, IRL Press, Oxford University Press, 1991]. This demonstrates that hydroxymethyl substituted RNA oligonucleotides (=RNA strands) and RNA complexes can be synthesised using known phosphoramidite derivatives using the standard techniques for RNA synthesis.

LNA is an oligonucleotide containing one or more 2'-O,4'-C-methylene-linked ribonucleotides (LNA nucleotides) [M. Petersen and J. Wengel, *Trends Biotechnol.* 2003, 21, 74-81]. LNA-modified siRNA is an siRNA construct containing one or more LNA monomers. Known methods have been used to incorporate LNA nucleotides into the RNA complexes to the invention by use of the commercially available LNA phosphoramidites [Pfundheller, Sørensen, Lomholt, Johansen, Koch and Wengel, J. "Locked Nucleic Acid Synthesis", *Methods Mol. Biol.* 2004, vol. 288 (Oligonucleotide Synthesis), 127-145, P. Herdewijn, Ed., Humana Press Inc.]

Hydroxymethyl substituted siRNA ("hydroxymethyl substituted small interfering RNA) is an siRNA construct containing one or more hydroxymethyl substituted nucleotide monomer (see FIG. 1 for structures of the hydroxymethyl substituted nucleotide monomer). The monomers exemplified are shown below:

Monomer C (C, T)

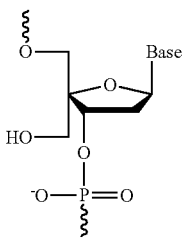

Monomer D (X)

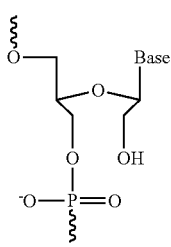

Oligonucleotides—Selected Antisense Strands in siRNA Constructs:

```
RNA      5'-ACU UGU GGC CGU UUA CGU CGC U
native

JW1103   5'-ACU UGU GGC CGU UUA CGU CG^L C^MeL U

JW1186   5'-ACU UGT GGC CGU UUA CGU CG^L C^MeL U

JW1187   5'-ACT UGT GGC CGU UTA CGT CG^L C^MeL U

W123     5'-ACU UGX GGC CGU UUA CGU CG^L C^MeL U

W124     5'-ACX UGU GGC CGU UUA CGU CG^L C^MeL U

W125     5'-ACU UGU GGC CGU UUA CGX CG^L C^MeL U

W126     5'-ACU UGU GGC CGX UUA CGU CG^L C^MeL U

W127     5'-ACU UGU GGC CGU UUA CGT CGX U

W128     5'-ACX UGU GGC CGU UUA CGT CGX U
```

Oligonucleotides—Selected Sense Strands in siRNA Constructs:

```
RNA      5'-GAC GUA AAC GGC CAC AAG UUC U
native

JW1104   5'-GAC GUA AAC GGC CAC AAG UT^L C^MeL U

JW1106   5'-GAC^MeL GUA AAC^MeL GGC CAC^MeL AAG
         UT^L C^MeL U

JW1188   5'-GAC GUA AAC GGC CAC AAG TTC

W043     5'-GAC GUA AAC GGC CAC AAG UTC U

W044     5'-GAC GTA AAC GGC CAC AAG UTC U

JW1189   5'-GAC GTA AAC GGC CAC AAG TTC

W129     5'-GAC GXA AAC GGC CAC AAG UT^L C^MeL U

W130     5'-GAC GXA AAC XGGC CAC AAG UT^L C^MeL U

W131     5'-GAC GUA AAC GGC CAC AAG UUX U

W132     5'-GAC GXA AAC GGC CAC AAG UUX U
```

Other hydroxymethyl substituted RNA stands that have been synthesised:

```
5'-ACU UGU GGC CGU UUA CGU CGC U

5'-GAC GTA AAC G

5'-GC CAC AAG UTC U
```

"L" in superscript indicates that the residue is an LNA nucleotide.

"MeL" in superscript indicates that the residue is an LNA nucleotide with a 5-methylcytosine base.

T in bold face underlined is a hydroxymethyl substituted nucleotide monomer. In this example it is the thymin-1-yl derivative of C4'-branched-RNA Monomer C (see FIG. 1).

C in bold face underlined is a hydroxymethyl substituted nucleotide monomer. In this example it is the 5-methylcytosin-1-yl derivative of C4'-branched-RNA Monomer C (see FIG. 1).

X in bold face underlined is a hydroxymethyl substituted acyclic nucleotide monomer. In the sequences above it is the uracil-1-yl derivative of 2',3'-seco-RNA Monomer D (see FIG. 1). In other examples and figures are other bases variants than uracil included.

See Examples 9 and 10 for further sequences studied.

Cellular studies (lung cancer cell line expressing EGFP) have been performed. As examples to illustrate the invention are used siRNA duplexes containing two or three nucleotide overhangs. This example design is only an illustration and many other constructs are included in the invention and works similarly. Thus are, for example, blunt ended siRNA duplexes, shorter or longer siRNA duplexes than the ones exemplified, and single stranded antisense strands included. Likewise are included RNA complexes comprising an antisense strand and a discontinued passenger strand (the "passenger strand" can also be called the "sense strand").

Example 2

Annealing and Transfection Procedure for siRNA Complexes of the Invention

Cells were plated in 6-well plates and grown on to 40-60% confluence. Immediately before transfection, the cells were re-plated in 1 ml of complete growth media per well. Sense and antisense strands where mixed in annealing buffer (10 mM Tris-HCl, pH 7.3, 50 mM NaCl) at 20 µM concentration of each and were incubated at 95° C. for 1 min and at 1 h at 37° C. Per well in a 6-well plate, the following solution was prepared: 4 µl of TransIT-TKO in 150 µl serum free RPMI media. Annealed siRNA complex was added, mixed carefully, incubated for 20 min at RT, and poured over the cells. The final RNA complex concentration was 50 nM. After 24 h incubation at 37° C., the media was changed and the cells were incubated for another 24 h at 37° C. The cells were removed by trypsination and split into half for subsequent RNA and flow analysis.

As gene silencing is achieved (see below), it is demonstrated that the RNA complexes of the invention containing hydroxylmethyl substituted monomers can penetrate a cell membrane under standard transfection conditions.

Example 3

Gene Silencing

Procedure for mRNA and protein quantification. Expression of eGFP protein was analysed by flow cytometric analysis. Western blotting was performed as follows: Cells were washed twice in PBS and an equal amount of cells were lysed in 2×SDS sample buffer [4% Sodium Dodecyl-Sulphate (SDS), 20% glycerol, 125 mM Tris/HCl pH 6.8, 0.01 mg/ml Bromphenol Blue, 10% 2-mercaptoethanol] at 90° C. for 2×10 min separated by gentle pippeting. Proteins were separated in an 8% SDS-acrylamide gel, and electro-blotted overnight onto a PVDF membrane (Immobilon). The filter was blocked for 1 h with PBS containing 10% w/v milk. EGFP protein was detected using a 1:1000 dilution of a rabbit polyclonal EGFP antibody (Santa Cruz Biotechnology). The mouse hnRNP C1 antibody was a gift from Seraphin Pinol-Roma. A horse radish peroxidase (hrp) conjugated secondary antibody (DAKO) was used with the ECL reagent (Amersham Biosciences) for visualization. eGFP mRNA was analysed by Northern blotting according to standard procedures.

The following is a list with results from gene silencing experiments conducted at 50 mM siRNA complex concentration. The results are given in percentages relative to the gene expression level obtained with a mis-matched control siRNA duplex (set at 100%):

| Entry | Sense/Antisense | Mean GFP | EGFP mRNA |
|---|---|---|---|
| 1 | RNA/RNA | 13% | 16% |
| 2 | JW1104/JW1103 | 13% | 28% |
| 3 | JW1188/JW1103 | 7% | 13% |
| 4 | JW1189/JW1103 | 6% | 15% |
| 5 | W043/JW1103 | | ~13% |
| 6 | W044/JW1103 | | ~19% |
| 7 | JW1104/JW1186 | 22% | 31% |
| 8 | JW1104/JW1187 | 62% | 90% |
| 9 | W131/W127 | 27% | |
| 10 | W132/W128 | 86% | |
| 11 | W131/W128 | 68% | |
| 12 | W132/W127 | 47% | |
| 13 | W129/JW1103 | 36% | |
| 14 | W130/JW1103 | 39% | |
| 15 | JW1106/W123 | 24% | |
| 16 | JW1106/W127 | 51% | |
| 17 | JW1106/W125 | 34% | |
| 18 | JW1106/W126 | 22% | |

Entry 1 shows that the unmodified siRNA complex is efficiently silencing the GFP gene.

Entry 2 shows that an LNA-modified siRNA complex is efficiently silencing the GFP gene. This construct has two LNA modifications towards the 3'-ends of the two RNA strands.

In the example gene silencing experiments of entries 3-8 are studied an siRNA complex containing C4'-branched-RNA hydroxymethyl substituted monomers of structure T/C (FIG. 3).

Entry 3 shows that an siRNA complex of the invention having a hydroxymethyl substituted monomer at positions 2 and 3 from the 3'-end of the sense strand is highly functional in silencing the GFP gene.

In the example of entry 3 and in the examples of entries 4, 5, 6, 13 and 14 is the antisense strand as an example an LNA-modified RNA strand, but an unmodified RNA antisense strand or a fully or partially modified RNA antisense strand would also be functional. The results obtained show that alternatively modified monomers like LNA monomers are fully compatible with the hydroxymethyl substituted monomers of the invention.

Entry 4 confirms that an siRNA complex of the invention having hydroxymethyl substituted monomers T/C in the sense strand is highly efficient in mediating gene silencing.

Entries 5 and 6 confirm that an siRNA complex of the invention having hydroxymethyl substituted monomers T/C in the sense strand is highly efficient in mediating gene silencing.

The results show that very efficient gene silencing is achieved with siRNA complexes of the invention having hydroxymethyl substituted monomers incorporated into the sense strand. The data show the surprising finding that in general even improved gene silencing is achieved with these RNA complexes of the invention when compared with the gene silencing achieved with unmodified siRNA or LNA-modified siRNA. Furthermore, silencing is efficient even with an RNA complex comprising a sense RNA strand with several hydroxymethyl substituted monomers in the central duplex forming core region (entry, W044 as example).

Entries 7 and 8 reveal that an siRNA complex of the invention having hydroxymethyl substituted monomers T/C in the antisense strand of the complex is able to mediate gene silencing. It seems that the more hydroxymethyl substituted monomers T/C that is incorporated into the antisense strand the lower the gene silencing activity.

An LNA-modified sense strand is used as an example in the examples of entries 7, 8, 15, 16, 17 and 18, but an unmodified RNA sense strand or a fully or partially modified RNA sense strand would also be functional. The results obtained show that alternatively modified monomers like LNA monomers are fully compatible with the hydroxymethyl substituted monomers of the invention.

In the example gene silencing experiments of entries 9-18 are studied an siRNA complex of the invention containing 2',3'-seco-RNA hydroxymethyl substituted monomer of structure X shown above in FIG. 3.

Entry 9 demonstrate that an siRNA complex of the invention having one hydroxymethyl substituted monomer X in each of the two RNA strands (towards the 3'-end of the two strands) mediate very efficient gene silencing to a level comparable to that of unmodified siRNA. This is surprising taking the non-cyclic nature of the ribose unit of the hydroxymethyl substituted monomer X into consideration.

With an additional X monomer in each of the two strands of the RNA complex, gene silencing efficiency is inefficient (entry 10).

Entry 11 reveals together with entry 10 that incorporation of a hydroxymethyl substituted monomer X close to the 5'-end of the antisense strand reduces the gene silencing efficiency of an siRNA complex.

Entry 12 reveals that incorporation of a hydroxymethyl substituted monomer X close to the 5'-end of the sense strand reduces the gene silencing efficiency of an siRNA complex when another monomer X is incorporated into the 3'-end of the sense strand.

Entries 13 and 14 confirm that incorporation of a hydroxymethyl substituted monomer X close to the 5'-end of the sense strand reduces the gene silencing efficiency of an siRNA complex. The results indicate that incorporation of a hydroxymethyl substituted monomer X in the central part of a sense strand of an siRNA construct is neither improving nor reducing gene silencing activity.

Entries 15-18 display results from gene silencing experiments with siRNA complexes of the invention comprising an LNA-modified RNA sense strand and antisense strands having one hydroxymethyl substituted monomer X.

The results show that siRNA complexes of the invention that contain hydroxymethyl substituted monomers X in the central region of the antisense strand, e.g. W126 and W123, mediate very efficient gene silencing. It is surprising that W127, which together with W131 mediates very efficient gene silencing, only induces moderate gene silencing with the LNA-modified RNA sense strand JW1106. This underlines the surprising aspect of the observation (entry 9) that an siRNA complex of the invention having one hydroxymethyl substituted monomer X in each of the two RNA strands (towards the 3'-ends of the two strands) mediate very efficient gene silencing to a level comparable to that of unmodified siRNA.

Results similar to the ones described above can be obtained with the RNA complexes of the invention containing hydroxymethyl substituted monomers having other nucleobases than uracil, thymine or 5-methylcytosine. For example can comparable gene silencing activities using similar protocols be obtained for the RNA complexes of the invention containing hydroxymethyl substituted monomers having adenine, cytosine or guanine as nucleobases.

Example 4

Immune Stimulation

Because the RNA complexes of the invention containing hydroxymethyl substituted monomers are chemically modified relative to the corresponding unmodified RNA complexes, they will display less immune stimulatory activity than the corresponding unmodified RNA complexes.

Example 5

Off-Target Effects

Because the RNA complexes of the invention containing hydroxymethyl substituted monomers can be modulated such that antisense-strand-modified siRNA complexes are inactive, gene silencing with less off-target effects is made possible by the invention. The key is to modify the sense strands with hydroxymethyl substituted monomers such that the sense strand cannot function as the antisense strand. This can e.g. be achieved by incorporating a hydroxymethyl substituted monomer towards the 5'-end of the sense strand.

With the acyclic monomer X reduced off-target effects can be achieved by incorporating monomer X in the antisense strand, most preferable around positions 6-8 from the 5'-end of the antisense strand, for example at position 7 from the 5'-end of the antisense strand.

Example 6

Synthesis of the RNA Complexes of the Invention Containing Functionalised and Conjugated Hydroxymethyl Monomers The hydroxymethyl substituent of the hydroxymethyl substituted monomers of the invention is functionalised by a conjugating group. A conjugating group is herein defined as a group that modulates, expands or improves the chemical, biophysical or biological properties of an RNA complex of the invention. Such groups may be useful for modulating cellular distribution, organ distribution, tissue distribution, melting temperatures, target affinities, biostability, signalling of hybridization etc.

Known methods can be used to convert a hydroxymethyl substituent into a variety of chemical derivatives [Furniss, Hannaford, Smith and Tatchell, Vogel's Textbook of Organic Chemistry, 1989, John Wiley & Sons]. This can be achieved at the nucleoside level, i.e. before conversion into a phosphoramidite derivative useful for automated RNA synthesis on an automated DNA synthesiser. After conversion of the hydroxymethyl group into a useful derivative, the phosphoramidite derivative needed for automated RNA synthesis is synthesised using standard methods, and incorporation of the derivatised or conjugated monomers into RNA oligonucleotides (strands) is subsequently achieved using standard methods (see Example 1).

Conjugation via an ether linkage. The hydroxymethyl substituent of the hydroxymethyl substituted monomers of the invention is functionalised by an ether linkage between a conjugating group and the methylene group of the hydroxymethyl substituent by a nucleophilic substitution reaction. This reaction involves conversion of the hydroxy group of the hydroxymethyl substituent into a good leaving group by e.g. mesylation or transformation into a halide, and subsequent nucleophilic attach by an alcohol or an alkoxide derivative.

Conjugation via a thioether linkage. The hydroxymethyl substituent of the hydroxymethyl substituted monomers of the invention is functionalised by a thioether linkage between a conjugating group and the methylene group of the hydroxymethyl substituent by a nucleophilic substitution reaction. This reaction involves conversion of the hydroxy group of the hydroxymethyl substituent into a good leaving group by e.g. mesylation or transformation into a halide, and subsequent nucleophilic attach by an alkylthiol or thioalkoxide derivative. If the nucleophile alternatively is SH$^-$, protection by e.g. acetylation leads to a phosphoramidite derivative that is useful for introduction of mercapto (SH) groups into the RNA complexes of the invention. As an alternative procedure to introduce a mearcapto functionality into the RNA complexes can conjugation with a disulfide containing moiety be used. After reduction of the disulfide containing RNA complex is the mercapto group functionalised RNA complex obtained.

Derivatisation into an aminomethyl group. The hydroxymethyl substituent of the hydroxymethyl substituted monomers of the invention can be converted into an aminomethyl group. This reaction involves conversion of the hydroxy group of the hydroxymethyl substituent into a good leaving group by e.g. mesylation or transformation into a halide, and subsequent nucleophilic attach by ammonia or a protected amine derivative (like e.g. phthalimide) that subsequently is deprotected (for example after RNA synthesis) to give the desired amino derivative. A trifluoroacetyl or Fmoc protecting group are other options for amino-protection during automated RNA synthesis, with liberation of a free amino group after standard oligonucleotide deprotection.

Conjugation via an amide linkage. The hydroxymethyl substituent of the hydroxymethyl substituted monomers of the invention is acting as a handle for attachment of amide-linked conjugating groups. This involves conversion of the hydroxy unit of the hydroxymethyl substituent into an amine unit, for example as described above, and further derivatisation of this amino group by e.g. a conjugating group via amide bond formation using known methods. This may take place before RNA synthesis or after RNA synthesis using methods known to a person skilled in the art [Bryld, Højland and Wengel, *Chem. Commun.* 2004, 1064; Mokhir, Tetzlaff, Herzberger, Mosbacher and Richart, *J. Comb. Chem.* 2001, 3, 374].

Conjugation via an amino linkage. The hydroxymethyl substituent of the hydroxymethyl substituted monomers of the invention is also acting as a handle for attachment of amino-linked conjugating groups. This involves conversion of the hydroxy unit of the hydroxymethyl substituent into an amine unit, for example as described above, and further derivatisation of this amino group by a conjugating group containing e.g. an aldehyde functionality by a reductive amination reaction which is a known reaction [Furniss, Hannaford, Smith and Tatchell, Vogel's Textbook of Organic Chemistry, 1989, John Wiley & Sons]. This may take place before RNA synthesis or after RNA synthesis.

Conjugation via a piperazino group or a linear diamino alkyl group. A piperazino group or a linear diamino alkyl group is also used for derivatisation by performing reactions as described [Bryld, Højland and Wengel, Chem. Commun. 2004, 1064-5]. These groups will be useful, as other conjugating groups can be attached at e.g. the distal nitrogen atom of a piperazino group (see FIG. 2, Monomer J) by e.g. amide bond formation or by a reductive amination reaction, either before or after RNA oligonucleotide synthesis [Bryld, Højland and Wengel, Chem. Commun. 2004, 1064; Mokhir, Tetzlaff, Herzberger, Mosbacher and Richart, J. Comb. Chem. 2001, 3, 374]. This way can e.g. cholesteryl or fatty acid units be linked to the RNA complexes of the invention via a piperazino-methyl substituent.

Using these procedures the RNA complexes of the invention can be prepared containing e.g. cholesteryl units, alkyl units, fatty acid units, polyamine derivatives, thio derivatives, amino acids, polypeptides, monosaccharide derivatives, polysaccharide derivatives or fluorophores, all connected to the RNA complexes of the invention via the methylene group of the hydroxymethyl substituent. The groups listed here are only examples of groups that can be attached using the procedures exemplified above. See FIG. 2 for structural examples of the conjugated monomers.

Example 7

Gene Silencing by the RNA Complexes of the Invention Containing Functionalised and Conjugated Hydroxymethyl Monomers Gene silencing is efficient with the RNA complexes of the invention containing the functionalised and conjugated hydroxymethyl monomers (see e.g. FIG. 2 or Example 6).

Efficient gene silencing is achieved when these functionalised and conjugated hydroxymethyl monomers are positioned at or close to the 3'-ends of the two strands of an siRNA complex.

Efficient gene silencing is furthermore achieved when these functionalised and conjugated hydroxymethyl monomers are positioned at or close to the 3'-end and the 5'-end of the sense strand of an siRNA complex.

Efficient gene silencing is in particular achieved when these functionalised and conjugated hydroxymethyl monomers are positioned at or close to the 3'-end of the sense strand of an siRNA complex.

Efficient gene silencing is furthermore achieved when these functionalised and conjugated hydroxymethyl monomers are positioned in a single stranded antisense RNA oligonucleotide.

Modulation of pharmacokinetic properties is achieved together with efficient gene silencing when the group (R in FIG. 2) of an RNA complex of the invention is a cholesteryl derivative. This leads for example to improved tissue distribution and cellular uptake, and also increased biostability.

Modulation of pharmacokinetic properties is achieved together with efficient gene silencing when the group (R in FIG. 2) of an RNA complex of the invention is a thio derivative. This leads to improved circulation time in a human body, i.e. reduced clearance via the kidneys.

Modulation of pharmacokinetic properties is achieved together with efficient gene silencing when the group (R in FIG. 2) of an RNA complex of the invention contains an amino group. This leads to improved tissue distribution.

Example 8

Biostability of the Hydroxymethyl-Substituted RNA Complexes

Experimental procedure for the stability assay. The hydroxymethyl substituted RNA complexes were incubated at 37° C. in 10% fetal bovine serum (Gibco) diluted in D-MEM (Gibco). Samples of 5 µl were collected at indicated time points and immediately frozen on dry ice in 15 µl 1.33× TBE/10% glycerol loading buffer and subjected to non-denaturing PAGE on a 15% gel. RNAs were visualised with SYBR gold (Invitrogen).

Such experiments show that the stability of the hydroxymethyl-substituted RNA complexes display improved stability in biological media relative to the native (or "unmodified") control RNA complexes. Thus the hydroxymethyl-substituted siRNAs are significantly more stable in 10% serum than ordinary siRNA. It can thus be envisioned that only a very small decline in hydroxymethyl-substituted siRNA size is observed over a more than one hour long incubation period. We conclude that the RNA complexes of the invention containing hydroxymethyl substituted monomers are very stable in cells, in animals and in humans, and that this characteristic is contributing to their very efficient gene silencing properties. Because of this pronounced biostability, the RNA complexes of the invention containing hydroxymethyl substituted monomers display gene silencing for a longer period of time than their unmodified counterparts.

Example 9

A Series of Gene Silencing Experiments Demonstrating the Strong Potential of Monomers of Structure D for Gene Silencing Using procedures described in the prior experiments were gene silencing studies conducted using siRNA duplexes of the sequences described earlier as well as of additional sequences (see FIGS. 4-9 for the sequences included in the studies of this example). These experiments included sequences containing one or more incorporations of monomer X (see Example 1 for description of monomer X). Monomer X is used herein only as an example structure and similar results are predicted for derivatives like e.g. monomer E, monomer F, monomer G, monomer I and monomer J (see FIG. 1 and FIG. 2). The bold and underlined monomers with a superscript L are LNA monomers. In this example, including FIGS. 4-9 are $\underline{\mathbf{C}^L} = \underline{\mathbf{C}^{MeL}}$=5-methylcytosin-1-yl LNA monomer.

The experiments for which the results are depicted in FIG. 4 all involve a sense strand that has two incorporations of monomer X (W130). It is shown that:
  it is possible to design a siRNA duplex composed of strands containing both hydroxymethyl-substituted and LNA monomers that display gene silencing functionality;
  it is possible to design a siRNA duplex composed of strand having a mismatched monomer X in the sense strand that display gene silencing functionality;
  the full RNA antisense strand (except for two LNA monomers toward the 3'-end) is well tolerated;
  a single X monomer is well tolerated in the antisense strand (W123, W125 or W126);

several X monomers are tolerated but less efficient gene silencing is observed with W186 and W187 than with W123, W125 or W126 as antisense strand;

significant gene silencing activity is seen with W188 though this antisense strand contains six LNA monomers which shows that a monomer X positioned centrally in an antisense strand is able to improve the gene silencing relative to the situation in which monomer X is substituted with the corresponding RNA monomer.

Figure 5:
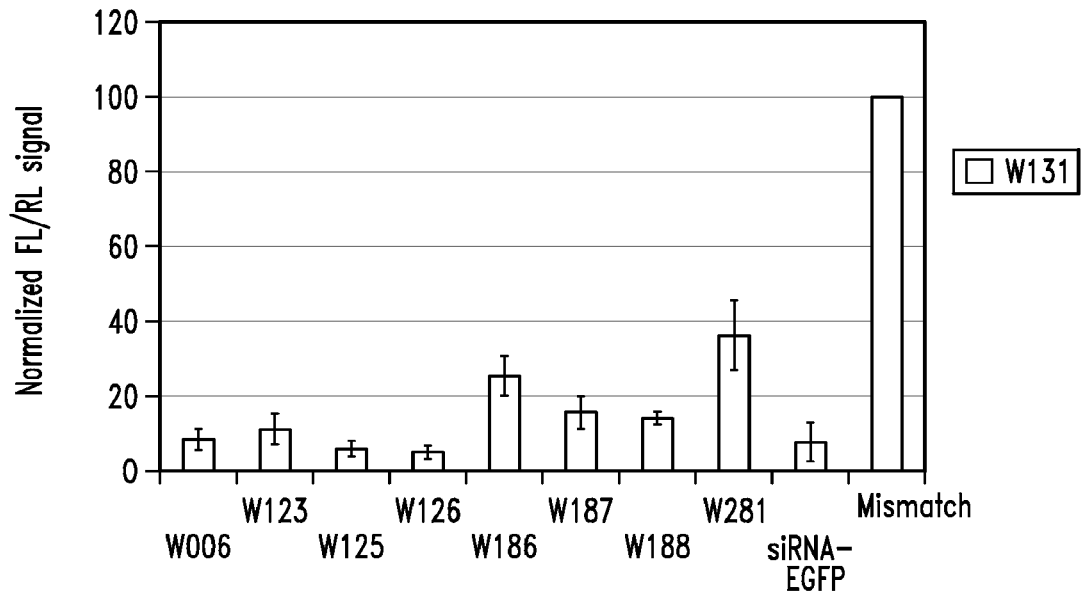

The experiments for which the results are depicted in FIG. 5 all involve a sense strand that has one monomer X positioned toward the 3'-end of the strand (W131). It is shown that:

the full RNA antisense strand (except for two LNA monomers toward the 3'-end) is well tolerated;
a single X monomer may be well tolerated in the antisense strand (W123);
a single X monomer might lead to as good or even improved gene silencing relative to the unmodified control (siRNA-EGFP) (W125 or W126);
several X monomers are rather well tolerated (W186, W187 or W281 as antisense strand);
significant gene silencing activity is seen with W188 though this antisense strand contains six LNA monomers which shows that a monomer X positioned centrally in an antisense strand is able to improve the gene silencing relative to the situation in which monomer X is substituted with the corresponding RNA monomer;
significant gene silencing is observed with several substitutions of monomer X in the antisense strand in a situation without the co-presence of LNA monomers (W281).

Figure 6:
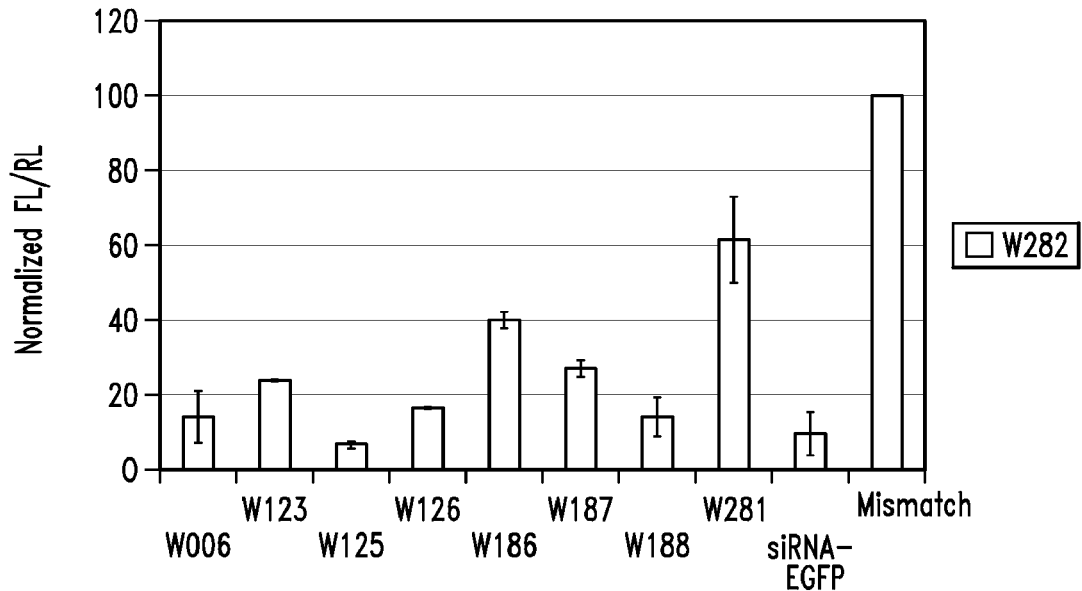

The experiments for which the results are depicted in FIG. 6 all involve a sense strand that has three X monomers dispersed along the sense strand (W282). It is shown that:

the full RNA antisense strand (except for two LNA monomers toward the 3'-end) is well tolerated;
a single X monomer may be well tolerated in the antisense strand, most so apparently toward the 3'-end for which as good or even improved gene silencing relative to the unmodified control (siRNA-EGFP) was observed (W123, W125, W126);
several X monomers are rather well tolerated (W186, W187 or W281 as antisense strand);
significant gene silencing activity is seen with W188 though this antisense strand contains six LNA monomers which shows that a monomer X positioned centrally in an antisense strand is able to improve the gene silencing relative to the situation in which monomer X is substituted with the corresponding RNA monomer, and that also when the sense strand contains several X monomers;
gene silencing is observed with several substitutions of monomer X in the antisense strand also in a situation without the co-presence of LNA monomers (W281).

Figure 7:
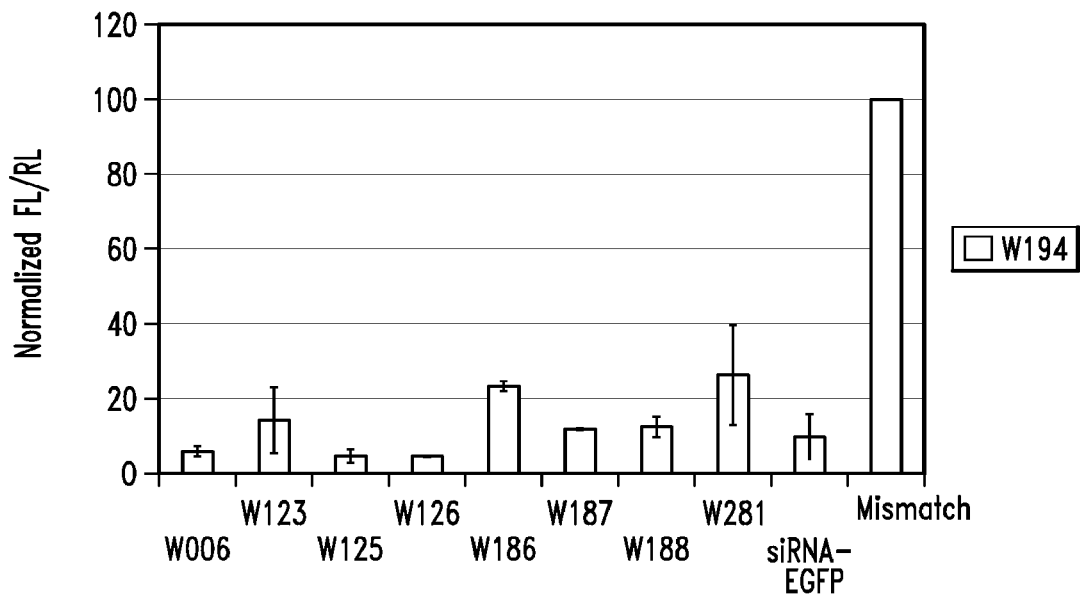

The experiments for which the results are depicted in FIG. 7 all involve a sense strand without monomer X (W194). It is shown that:

a single X monomer may be well tolerated in the antisense strand (W123);
a single X monomer might lead to as good or even improved gene silencing relative to the unmodified control (siRNA-EGFP) (W125 or W126);
several X monomers are rather well tolerated (W186, W187 or W281 as antisense strand);
significant gene silencing activity is seen with W188 though this antisense strand contains six LNA monomers which shows that a monomer X positioned centrally in an antisense strand is able to improve the gene silencing relative to the situation in which monomer X is substituted with the corresponding RNA monomer;
significant gene silencing is observed with several substitutions of monomer X in the antisense strand also in a situation without the co-presence of LNA monomers (W281).

Figure 8:
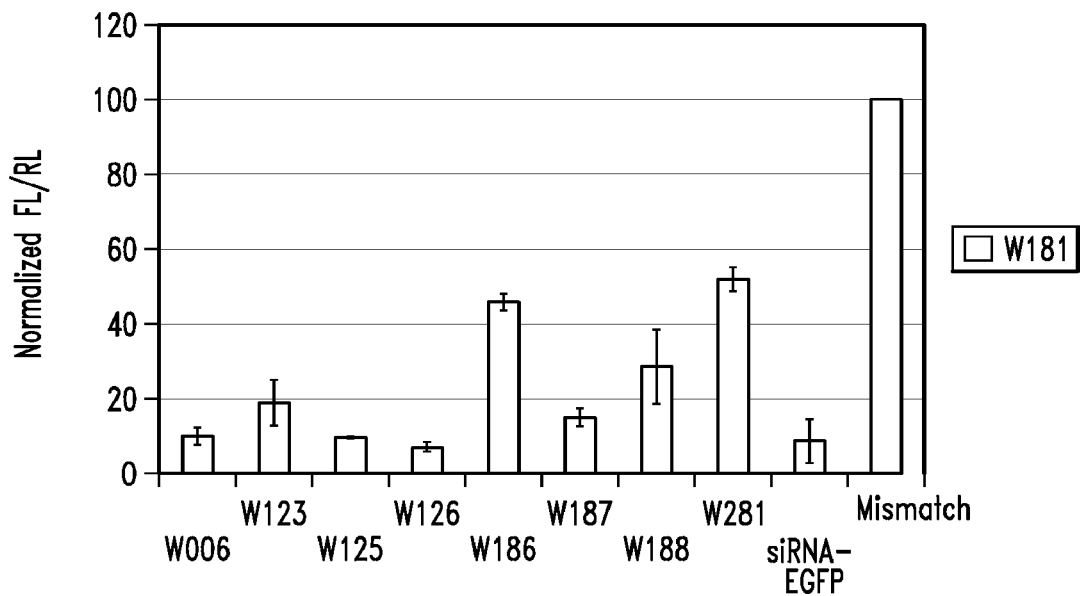

The experiments for which the results are depicted in FIG. 8 all involve a sense strand without monomer X (W181) but with four LNA monomers incorporated in the duplex forming segment (plus two LNA monomers in the 3'-end). It is shown that:

a single X monomer is well tolerated in the antisense strand (W123, W125 or W126);
several X monomers are rather well tolerated (W186, W187 or W281 as antisense strand);
significant gene silencing activity is seen with W188 though this antisense strand contains six LNA monomers which shows that a monomer X positioned centrally in an antisense strand is able to improve the gene silencing relative to the situation in which monomer X is substituted with the corresponding RNA monomer;
significant gene silencing is observed with several substitutions of monomer X in the antisense strand also in a situation without the co-presence of LNA monomers (W281).

Figure 9:
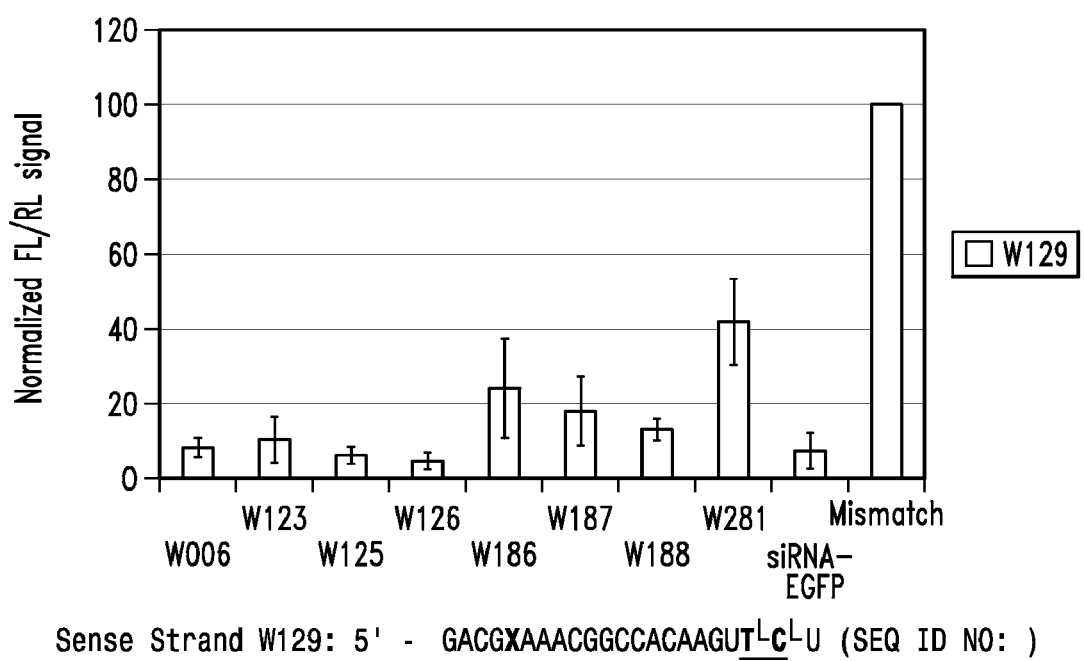

The experiments for which the results are depicted in FIG. 9 all involve a sense strand that has one monomer X positioned toward the 5'-end of the strand (W129). It is shown that:

the full RNA antisense strand (except for two LNA monomers toward the 3'-end) is well tolerated;
a single X monomer may be well tolerated in the antisense strand and might lead to improved gene silencing relative to the unmodified control (siRNA-EGFP) (W123, W125 or W126);
several X monomers are rather well tolerated (W186, W187 or W281 as antisense strand);
significant gene silencing activity is seen with W188 though this antisense strand contains six LNA monomers which shows that a monomer X positioned centrally in an antisense strand is able to improve the gene silencing relative to the situation in which monomer X is substituted with the corresponding RNA monomer;
significant gene silencing is observed with several substitutions of monomer X in the antisense strand in a situation without the co-presence of LNA monomers (W281).

The data shown below indicate that hydroxymethyl-substituted monomers are compatible with the sisiRNA approach. As an example, the use of the tri-molecular combination of the W123 antisense strand+(W004+W005) sense strands leads to efficient gene silencing (i.e., "siRNA effect" has a low value, in the case of the siRNA effect is 0.24) which shows that monomer X may be positioned in the antisense strand of sisiRNA complexes (compare to Control; read out 1.0). Data for unmodified siRNA is also shown. The design of the antisense strand is important, as the combination of the W186 antisense strand+(W004+W005) sense strands is unable to induce a gene silencing effect. This shows that the number of hydroxymethyl-substituted monomers (e.g. Monomer D) should be low, and most favourably restricted to one monomer (besides optional hydroxymethyl-substituted monomers in the overhang of the antisense strand). Other RNA complexes included in the study depicted in FIG. 9 are equally efficient with respect to gene silencing.

| Antisense strand | siRNA effect |
|---|---|
| W123 | 0.24 |
| W125 | 0.26 |
| W126 | 0.23 |
| W186 | 1.12 |
| SiRNA | 0.11 |
| Control | 1.0 |

Example 10

Seed Modifications Reduce Off-Target Effects

Using antisense strand W124, and W207 (5'-GAC GUA AAC GGC CAC AAG UT$^{LC^{MeL}}$) (SEQ ID NO:) as sense strand in an siRNA duplex at 50 nM concentration, we have shown that the monomer X when present in the so-called seed-region of the antisense strand has a selectivity enhancing effect which will lead to less off-target effects. The experimental setup thus allowed discrimination between siRNA effect (gene silencing with strand cleavage) and miRNA effect (translational repression; plasmid-based off-target sensor having four target regions composed of only seed region matching). Using the combination above, the siRNA effect was as for the unmodified siRNA control whereas the miRNA effect was significantly reduced. A similar effect was obtained for the siDharma (a commercial product having a 2'-O-Me-RNA monomer incorporated in position no. 2 from the 5'-end of the antisense strand). As stated above this shows that a hydroxymethyl-substituted monomer (e.g. Monomer D) present in the so-called seed region of the antisense strand leads to a favourable effect (i.e., reduced or elimination of off-target effect). Thus, a method for reducing or eliminating off-target effect of an RNA complex, the method comprising incorporating one or more hydroxymethyl-substituted monomers (e.g. Monomer D) in an RNA complex or preparing an RNA complex containing one or more hydroxymethyl-substituted monomers (e.g. Monomer D). See table below for the results for gene silencing (i.e., "siRNA effect") and off-target effect (i.e., "miRNA effect"). These data indicate that an RNA complex containing one or more hydroxymethyl-substituted monomers (e.g., Monomer D) reduce the expression of the target while minimizing off-target effect.

| Antisense strand | siRNA effect | miRNA effect |
|---|---|---|
| W124 | 0.12 | 0.38 |
| W125 | 0.04 | 0.19 |
| SiRNA | 0.06 | 0.15 |
| siDharma | 0.08 | 0.37 |
| Control | 1.0 | 1.0 |

For further seed walk studies, we have prepared the following sequences composed of RNA monomers (rA, rC, rG and rU) and hydroxymethyl-modified monomers (Monomer D; labeled sA, sC, sG and sU for the adenin-9-yl, cytosin-1-yl, guanin-9-yl and uracil-1-yl derivatives, respectively). Monomer X represents Monomer D with a nucleobase:

The numbering of the first nine oligonucleotides shown below are as follows (from no. 1 from the top-no. 9):

| W313; W314; W315; W316; W317; W123; W318; W319 and W320 |
|---|
| sA rC rU rU rG rU rG rG rC rC rG rU rU rU rA rC rG rU rC lG lC rU |
| rA sC rU rU rG rU rG rG rC rC rG rU rU rU rA rC rG rU rC lG lC rU |
| rA rC sU rU rG rU rG rG rC rC rG rU rU rU rA rC rG rU rC lG lC rU |
| rA rC rU sU rG rU rG rG rC rC rG rU rU rU rA rC rG rU rC lG lC rU |
| rA rC rU rU sG rU rG rG rC rC rG rU rU rU rA rC rG rU rC lG lC rU |
| rA rC rU rU rG sU rG rG rC rC rG rU rU rU rA rC rG rU rC lG lC rU |
| rA rC rU rU rG rU sG rG rC rC rG rU rU rU rA rC rG rU rC lG lC rU |
| rA rC rU rU rG rU rG sG rC rC rG rU rU rU rA rC rG rU rC lG lC rU |
| rA rC rU rU rG rU rG rG sC rC rG rU rU rU rA rC rG rU rC lG lC rU |
| sA rC rU rU rG rU rG rG rC rC rG rU rU rU rA rC rG rU rC rG sU rU |
| rA sC rU rU rG rU rG rG rC rC rG rU rU rU rA rC rG rU rC rG sU rU |
| rA rC sU rU rG rU rG rG rC rC rG rU rU rU rA rC rG rU rC rG sU rU |
| rA rC rU sU rG rU rG rG rC rC rG rU rU rU rA rC rG rU rC rG sU rU |
| rA rC rU rU sG rU rG rG rC rC rG rU rU rU rA rC rG rU rC rG sU rU |
| rA rC rU rU rG sU rG rG rC rC rG rU rU rU rA rC rG rU rC rG sU rU |
| rA rC rU rU rG rU sG rG rC rC rG rU rU rU rA rC rG rU rC rG sU rU |
| rA rC rU rU rG rU rG sG rC rC rG rU rU rU rA rC rG rU rC rG sU rU |
| rA rC rU rU rG rU rG rG sC rC rG rU rU rU rA rC rG rU rC rG sU rU |

By using similar experimental techniques as described in previous examples with oligomers W313; W314; W315; W316; W317; W123; W318; W319 and W320 as antisense strand and oligomer JW1104 as sense strand in gene silencing experiments is was shown that the potency of the siRNA constructs containing the hydroxymethyl-substituted monomer D can be improved relative to unmodified siRNA or a commercial chemically modified siRNA product (Dharma) having a 2'-O-Me-RNA monomer in position no. 2 from the 5'-end of the antisense strand). Further, siRNA complexes containing 2',3'-seco-RNA Monomer D showing that this monomer can be incorporated in siRNA constructs such that off-target effects (miRNA effects) are reduced relative to the reference unmodified siRNA (SiRNA)

The results for 1 nM, 10 nM and 100 nM RNA complexes are depicted in tabular form below (Control; data adjusted to 1.0). Gene silencing via siRNA and miRNA (microRNA) effects were studied at various concentrations of the different siRNA duplexes as indicated. Similar results are expected from strands like the nine strands shown above containing exclusively RNA and acyclic 2',3'-seco-RNA monomers.

Hydroxymethyl-modified monomer D as antisense strand modification reduces off-target effects and increases potency of gene silencing.

|  | SiRNA effect | | | miRNA effect | |
| --- | --- | --- | --- | --- | --- |
|  | 1 nm | 10 nm | 100 nm | 1 nm | 10 nm |
| W313 | 0.45 | 0.76 | 0.81 | 0.52 | 0.67 |
| W314 | 0.58 | 0.96 | 0.88 | 0.72 | 0.64 |
| W315 | 0.48 | 0.82 | 0.85 | 0.62 | 0.64 |
| W316 | 0.46 | 0.75 | 0.78 | 0.85 | 0.97 |
| W317 | 0.26 | 0.32 | 0.92 | 0.39 | 0.52 |
| W318 | 0.17 | 0.18 | 0.45 | 0.46 | 0.62 |
| W319 | 0.34 | 0.50 | 0.66 | 0.23 | 0.29 |
| W320 | 0.87 | 0.96 | 0.97 | 0.13 | 0.12 |
| Dharma | 0.52 | 0.47 | 0.89 | 0.37 | 0.40 |
| SiRNA | 0.23 | 0.24 | 0.54 | 0.12 | 0.14 |
| Control | 1.0 | 1.0 | 1.0 | 1.0 | 1.0 |

The design is important, and the most potent of the above mentioned series of oligomers for siRNA effect is W318 which has a hydroxymethyl-substituted monomer D at position no. 7 from the 5'-end of the antisense strand. W318 also leads to favorably low off target (miRNA) effects relative to unmodified siRNA or a commercial product (Dharma). In general the use of the antisense strands listed above having a hydroxymethyl-substituted monomer D incorporated leads to favorably low off target (miRNA) effects. Importantly and surprisingly, high potency and low off target effects can simultaneously be realised using a construct with an antisense strand containing a hydroxymethyl-substituted monomer D (see table above). In particular the design of W318 is favorable showing that a hydroxymethyl-substituted monomer D can favorably be incorporated around the boarder of the so-called seed region of the antisense strand, most favorably around positions no. 5-10 from the 5'-end of the antisense strand, like e.g. position no. 7 from the 5'-end of the antisense strand. Additional incorporations of one or more hydroxymethyl-substituted monomer D can be realised in the two strands.

It can furthermore be note that the effect can be reversed if monomer X is positioned in the antisense strand around positions 9-16, wherein the positions are counted from the 5' end. If for example monomer X in the antisense strand is present in position no 9 from the 5'-end of the antisense strand, the antisense strand and the duplex acts as a microRNA (the siRNA effect will be minimal and the microRNA effect much higher). This effect possibly stems from the reduced tendency towards full length binding because of reduced affinity caused by the presence of an acyclic hydroxymethyl substituted monomer X (=monomer D).

Example 11

Synthesis of Phosphoramidite Monomeric Building Blocks

The scheme below displays procedures that have been conducted in order to exemplify synthesis of monomeric amidite (=phosphoramidite) building blocks:

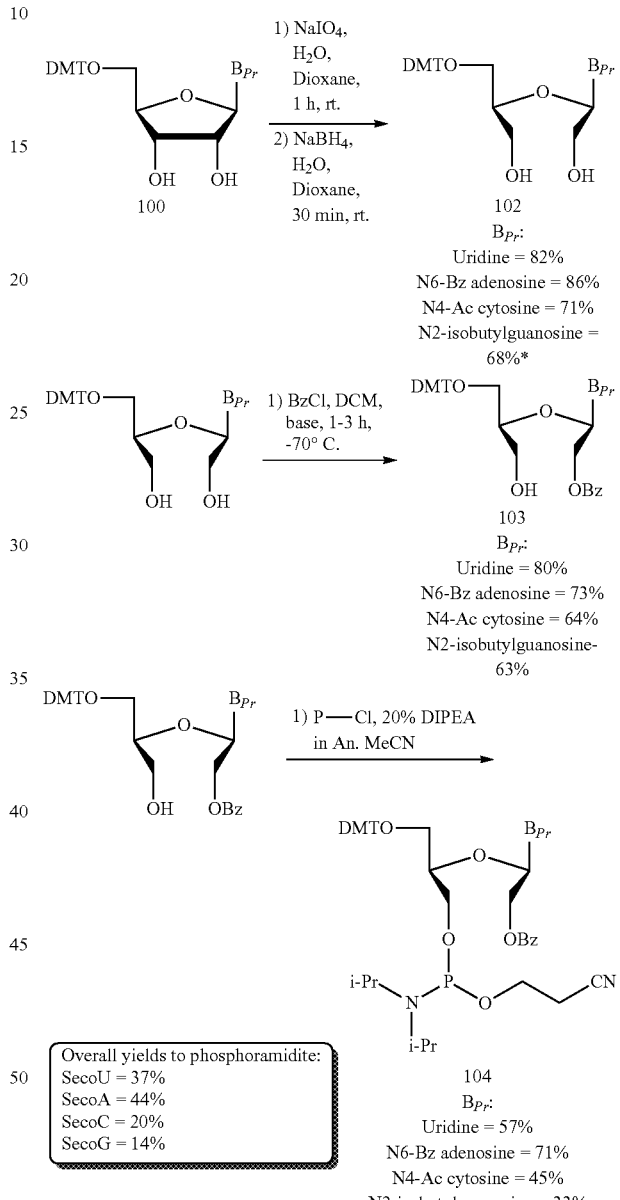

*The ringopening step to give SecoG and SecoC was done without purification after the DMT protection, the written yields are therefor overall yeilds of the two steps.

Compounds 100 are ribonucleoside starting materials. Compounds 102 are diols prepared by oxidative cleavage reactions followed by reduction. Compounds 103 are O2'-benzoylated derivatives prepared by selective benzoylation of the O2'-hydroxy group of compounds 102. Compounds 104 are amidites (=phosphoramidites) prepared by O3'-phosphorylation of the O3'-hydroxy group of compounds 103. Below are detailed procedures and characterization data included as example procedures.

5'-O-(4,4'-Dimethoxytrityl)-2',3'-secouridine (102-U)

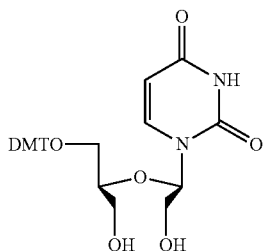

Nucleoside 100-U (5'-O-(4,4'-Dimethoxytrityl)uridine; 10.35 g, 18.94 mmol) was dissolved in dioxane (250 mL) and water (50 mL). $NaIO_4$ (4.47 g, 20.90 mmol) was dissolved in water (50 mL) and added to the dissolved nucleoside. The mixture was stirred for 1 h, during which a white precipitate was formed. Additional dioxane (200 mL) was added and the suspension was stirred for 15 min, whereupon the suspension was filtered through a glass filter and the filter cake was washed with dioxane (100 mL). The filtrates were combined, $NaBH_4$ (797 mg, 21.1 mmol) was added and the reaction mixture stirred for 30 min. The reaction mixture was neutralized with a buffer (pyridine:AcOH 1:1, v/v, ~10 mL). After evaporation of the mixture to approximately 150 mL $CH_2Cl_2$ (100 mL) was added and the mixture washed with sat. aq. $NaHCO_3$ (2×100 mL). The organic phase was separated, dried with $Na_2SO_4$, evaporated to dryness, and the resulting residue was purified by column chromatography (40% acetone in petroleum ether) affording the desired nucleoside 102-U as a white foam after evaporation of the solvents.

Yield: 8.53 g (82%).

$R_f$: 0.2 (10% MeOH in $CH_2Cl_2$).

$^1H$ NMR (DMSO-$d_6$): δ 11.34 (br s, NH), 7.62 (d, 1H, J=8.05 Hz, H6), 7.45-7.15 (m, 9H, ar), 6.85 (d, 4H, ar), 5.80 (t, 1H, J=6.2 Hz, H1'), 5.52 (d, 1H, J=8.05 Hz, H5), 5.12 (t, 1H, J=5.86 Hz, 2'OH), 4.74 (t, 1H, J=5.49 Hz, 3'OH), 3.72 (s, 6H, $OCH_3$), 3.55-3.47 (m, 3H, H2'/H4'), 3.40 (t, 2H, J=5.13 Hz, H3'), 3.01-2.90 (m, 2H, H5').

$^{13}C$ NMR (DMSO-$d_6$): δ 163.2, 157.9, 151.4, 144.8, 141.1 (C5), 135.4, 129.5 (ar), 127.7, 127.5 (ar), 126.5 (ar), 113.0, 101.6 (C6), 85.3, 83.6 (C1'), 79.3 (C2'/C4'), 63.5 (C5'), 61.1, 60.5 (C2'/C4'), 54.9 ($—OCH_3$).

ESI-HiRes (mNa$^+$): m/z: 571.1743 calc.: 571.2051.

2'-O-Benzoyl-5'-O-(4,4'-dimethoxytrityl)-2',3'-secouridine (103-U)

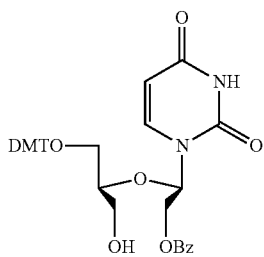

Nucleoside 102-U (3.01 g, 5.50 mmol) was coevaporated with an. toluene (15 mL). The resulting residue was dissolved in an. DCM (150 mL) along with an. Pyr. (4.4 mL) and the mixture was cooled to −70° C. Benzoyl chloride (700 μL, 6 mmol) was slowly added to the reaction mixture and stirred for 1 h at −70° C. EtOH (5 mL) was added to the solution and subsequently allowed to reach rt. The reaction mixture was washed with sat. aq. $NaHCO_3$ (3×100 mL) and brine (100 mL). The combined aqueous phase was back extracted with $CH_2Cl_2$ (100 mL). The organic phases were combined and evaporated. The resulting residue was purified by column chromatography (3.5% MeOH in DCM) affording the product 103-U as a white foam after evaporation of the solvents.

Yield: 3.44 g (79%).

$R_f$: 0.3 (5% MeOH in $CH_2Cl_2$).

$^1H$ NMR (DMSO-$d_6$): δ11.43 (s, 1H, NH, ex), 7.93-7.87 (m, 2H, ar), 7.80 (d, 1H, J=8.05 Hz, H6), 7.70-7.63 (m, 1H), 7.56-7.48 (m, 2H, ar), 7.35-7.17 (m, 10H, ar), 6.89-6.81 (m, 4H, ar), 6.20 (t, 1H, J=5.49 Hz, H1'), 5.56 (d, 1H, J=8.05 Hz, H5), 4.83 (t, 1H, OH-3', ex), 4.58 (dq, 2H, H2'), 3.73 (s, 7H, $—OCH_3$), 3.70-3.62 (m, 1H, H4'), 3.45 (t, 2H, H3'), 3.11-2.96 (m, 2H, H5').

$^{13}C$ NMR (DMSO-$d_6$): δ 164.92, 162.98, 157.89, 151.00, 144.67, 140.51, 135.45, 135.35, 133.54, 129.49, 129.45, 129.13, 129.02, 128.92, 128.74, 128.61, 127.65, 127.51, 126.49, 113.16, 113.01, 102.06, 85.35, 80.84, 79.57, 71.8, 71.8, 63.4, 60.5, 54.9, 54.8.

ESI-HiRes (mNa$^+$): m/z: 675.1949 calc.: 675.2313.

2'-O-Benzoyl-3'-O-(2-cyanoethoxy(diisopropylamino)phosphino)-5'-O-(4,4'-dimethoxytrityl)-2',3'-secouridine (104-U)

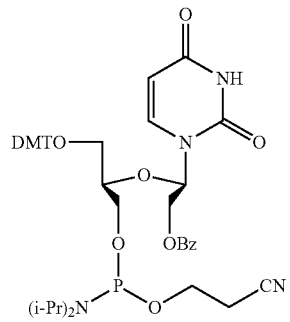

Nucleoside 103-U (679 mg, 1.04 mmol) was coevaporated with DCE (3×6 mL) and dried for 12 h in vacuo. The residue was dissolved in 20% DIPEA in MeCN (6.5 mL) and the mixture was stirred. 2-Cyanoethyl-N,N-diisopropylchlorophosphoramidite [P(Cl)($OCH_2CH_2CN$)(N(iPr)$_2$): 0.66 mL, 3.02 mmol] was added to the reaction mixture and stirring was continued for 40 min. The reaction mixture was poured into DCE (10 mL) and washed with sat. aq. $NaHCO_3$ (10 mL) and the aqueous phase was back extracted with DCE (10 mL). The organic phases were pooled and evaporated to afford white foam. The crude product was purified by column chromatography (0-20% EtOAc in toluene) to give nucleoside 104-U as a white solid material after evaporation of the solvents.

Yield: 600 mg (68%).

$R_f$: 0.6 (50% EtOAc in toluene).

$^{31}P$ NMR (MeCN): δ 147.8.

ESI-HiRes (mNa$^+$): m/z: 875.2946 calc.: 875.3391.

6-N-Benzoyl-5'-O-(4,4'-dimethoxytrityl)-2',3'-secoadenosine (102-A)

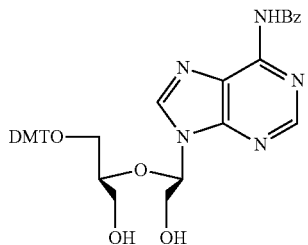

6-N-Benzoyl-5'-O-(4,4'-Dimethoxytrityl)adenosine (100-A; 7.02 g, 10.42 mmol) was dissolved in dioxane (150 mL) and water (25 mL). NaIO$_4$ (2.73 g, 11.77 mmol) was dissolved in water (25 mL) and added to the dissolved nucleoside. The mixture was stirred for 1 h, during which a white precipitate was formed. Additional dioxane (100 mL) was added and the suspension was stirred for 15 min, whereupon the suspension was filtered through a glass filter and the filter cake washed with dioxane (50 mL). The filtrates were combined, NaBH$_4$ (435 mg, 11.5 mmol) was added and the reaction mixture stirred for 30 min. Acetone was then added to quench residual NaBH$_4$. The reaction mixture was neutralized with a buffer (pyridine:AcOH 1:1, v/v, ~10 mL). The reaction mixture was reduced to approximately 100 mL and CH$_2$Cl$_2$ (100 mL) was added and the mixture washed with sat. aq. NaHCO$_3$ (2×100 mL). The organic phase was separated, dried with Na$_2$SO$_4$, evaporated to dryness, and the resulting residue was purified by column chromatography using DCM and i-PrOH to give the product as a white solid material after evaporation of the solvents.

Yield: 6.07 g (86%).
R$_f$: 0.22 (5% i-PrOH in DCM).
$^1$H NMR (DMSO-d$_6$): δ 11.23 (br s, 1H, N6H), 8.76 (s, 1H, adenin C8/C2), 8.68 (s, 1H, adenin C8/C2), 8.07 (d, 2H, J=6.96 Hz, Ar), 7.69-7.50 (m, 3H, Ar), 7.25-6.91 (m, 9H, Ar), 6.79 (dd, 4H, Ar), 6.06 (t, 1H, H1'), 5.29 (t, 1H, 2'OH), 4.84 (t, 1H, 3'OH), 4.19-4.02 (m, 2H, H2'), 3.90-3.80 (m, 1H, H4'), 3.69 (s, 6H, 2×—OCH$_3$), 3.49 (t, 2H, H3'), 2.93-2.74 (m, 2H, H5').
$^{13}$C NMR (DMSO-d$_6$): δδ 165.6, 157.9, 152.8, 151.6 (adenin CH), 150.2, 144.6, 143.1 (adenin CH), 135.7, 135.4, 132.4 (Ar), 129.4 (Ar), 128.5 (Ar), 128.4 (Ar), 127.7 (Ar), 127.5 (Ar), 126.4 (Ar), 125.2, 113.0 (Ar), 85.0, 84.5 (1'C), 79.6 (4'C), 63.6 (5'C), 61.4 (2'C), 60.9 (3'C), 54.9 (—OCH$_3$).

6-N-Benzoyl-2'-O-benzoyl-5'-O-(4,4'-dimethoxytrityl)-2',3'-secoadenosine (103-A)

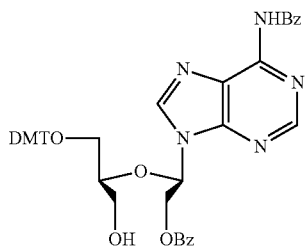

Nucleoside 102-A (2.01 g, 2.98 mmol) was coevaporated with an. MeCN (2×30 mL) and dried overnight. The resulting residue was dissolved in an. DCM (150 mL) along with an. DBU (900 mg, 5.96 mmol) and the mixture was cooled to −70° C. 0.5 M benzoyl chloride solution (6.56 mL, 3.28 mmol) was slowly added to the reaction mixture. The reaction mixture was stirred for 1 h at −70° C. and subsequently allowed to reach rt whereupon EtOH (5 mL was added). The reaction mixture was washed with sat. aq. NaHCO$_3$ (3×150 mL) and brine (150 mL). The combined aqueous phase was back-extracted with CH$_2$Cl$_2$ (100 mL). The organic phases were combined and evaporated. The resulting residue was purified by column chromatography (0-100% EtOAc in petroleum ether) affording the product nucleoside 103-A as a white foam after evaporation of the solvents.

Yield: 1.69 g (73%).
R$_f$: 0.49 (EtOAc).
$^1$H NMR (DMSO-d$_6$): δ 11.28 (s, 1H, NH), 8.82 (s, 1H, adenine CH), 8.76 (s, 1H, adenine CH), 8.06 (d, 2H, Ar), 7.79 (d, 2H, Ar), 7.55-7.40 (m, 6H, Ar), 7.25-6.89 (m, 10H, Ar), 6.77 (dd, 4H, Ar), 6.51 (t, 1H, H1'), 4.99 (m, 2H, H2'), 4.91 (t, 1H, 3'OH), 3.89 (ap. s, 1H, H4'), 3.72 (s, 6H, 2×—OCH$_3$), 3.54 (m, 2H, H3'), 2.81 (m, 2H, H5').
$^{13}$C NMR (DMSO-d$_6$): δ 165.0, 157.9, 152.4, 150.5, 144.6, 142.9 (Adenine CH), 135.6, 133.6 (Ar), 132.4 (Ar), 129.0 (Ar), 128.8 (Ar), 128.4 (Ar), 127.5 (Ar), 125.2 (Ar), 113.0 (Ar), 85.1, 81.5 (C1'), 79.9 (C4'), 63.8 (C2'), 63.5, 54.9 (—OCH$_3$).
ESI-HiRes (mNa$^+$): m/z: 802.2848 calc.: 802.2847.

6-N-Benzoyl-2'-O-benzoyl-3'-O-(2-cyanoethoxy(diisopropylamino)phosphino)-5'-O-(4,4'-dimethoxytrityl)-2',3'-secoadenosine (104-A)

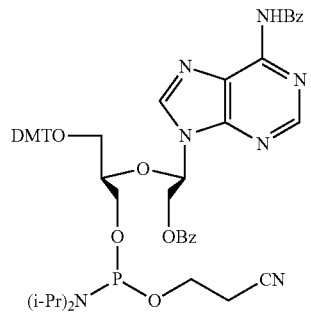

Nucleoside 103-A (1.69 g, 2.17 mmol) was coevaporated with an. MeCN (2×20 mL) and dried for 12 h in vacuo. The residue was dissolved in 20% DIPEA in MeCN (40 mL) and the resulting mixture was stirred. 2-Cyanoethyl-N,N-diisopropylchlorophosphoramidite [P(Cl)(OCH$_2$CH$_2$CN)(N(iPr)$_2$); 1.0 mL] was added to the reaction mixture which was stirred for 40 min. Additional 2-Cyanoethyl-N,N-diisopropylchlorophosphoramidite (0.2 mL) was added and the resulting mixture was stirred for 3 hours. EtOH (5 mL) was added and the mixture was washed with sat. aq. NaHCO$_3$ (3×50 mL) and the aqueous phase was back-extracted with DCM (50 mL). The organic phases were pooled and evaporated. The crude product was purified by column chromatography (0-100% EtOAc in petroleum ether) to afford white foam after evaporation of the solvents.

Yield: 1.52 g (71%).
R$_f$: 0.75 (5% MeOH in DCM).
$^{31}$P NMR (MeCN): δ 148.9.
ESI-HiRes (mNa$^+$): m/z: 1002.3885 calc.: 1002.3926.

4-N-Acetyl-5'-O-(4,4'-dimethoxytrityl)-2',3'-secocytidine (102-C)

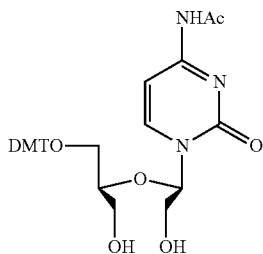

4-N-Acetylcytidine (11.75 g, 41.18 mmol) was coevaporated with an. pyr (50 mL). The resulting residue was dissolved in an. pyr (160 mL). DMT-Cl (4,4'-dimethoxytritylchloride; 16.76 g, 49.42 mmol) was added as a solid material and the resulting mixture was stirred for 2 hours at rt. The reaction mixture was washed with sat. aq. NaHCO$_3$ (3×50 mL), and the organic phase was evaporated to yield a white foam which was dried. This residue was dissolved in dioxane (500 mL) and water (100 mL). NaIO$_4$ (10.62 g, 49.5 mmol) was dissolved in water (100 mL) and added to the dissolved nucleoside. The mixture was stirred for 1 h during which time a white precipitate was formed. Additional 400 mL dioxane was added and stirring was continued for 15 min. The precipitate was filtered of and washed with dioxane (200 mL). The filtrates were combined and NaBH$_4$ (1720 mg, 45.5 mmol) was added, and stirring was continued for 30 min. To neutralize the reaction mixture, a buffer (10 mL, 1:1—AcOH: pyridine) was added until pH 7 was reached. The reaction mixture was evaporated to 300 mL and extracted with EtOAc (150 mL). The organic phase was washed with sat. aq. NaHCO$_3$ (3×200 mL) and evaporated. The residue was purified by column chromatography with a gradient of MeOH in EtOAc to give the product as a white solid material after evaporation of the solvents.

Yield: 17.24 g (71%).

R$_f$: 0.19 (5% MeOH in CHCl$_3$).

$^1$H NMR (DMSO-d$_6$): δ 10.94 (s, 1H, NH), 8.08 (d, 1H, J=7.32 Hz, Cytidine CH), 7.31-7.12 (m, 12H, Ar/Cytidine CH), 6.85 (d, 4H, Ar), 5.96 (t, 1H, H1'), 5.13 (t, 1H, 2'OH), 4.74 (t, 1H, 3'OH), 3.73 (s, 6H, 2×—OCH$_3$), 3.63 (m, 3H, H2'/H4'), 3.43 (m, 2, H3'), 3.00 (m, 2H, H5'), 2.13 (s, 3H, —CH$_3$).

$^{13}$C NMR (DMSO-d$_6$): δ 170.9, 162.3, 158.0, 155.4, 146.1 (Cytidine C5/C6), 144.6, 135.6, 129.6 (ar), 127.7 (ar), 126.6 (ar), 113.1 (ar), 95.4 (Cytidine C5/C6), 85.5, 84.7 (C1'), 79.4 (C2'/C4'), 63.8 (C5'), 61.7 (C2'/C4'), 60.5 (C3'), 55.0 (—OCH$_3$), 24.3 (—CH$_3$).

ESI-HiRes (mNa$^+$): m/z: 612.2298 calc.: 612.2316.

4-N-Acetyl-2'-O-benzoyl-5'-O-(4,4'-dimethoxytrityl)-2',3'-secocytidine (103-C)

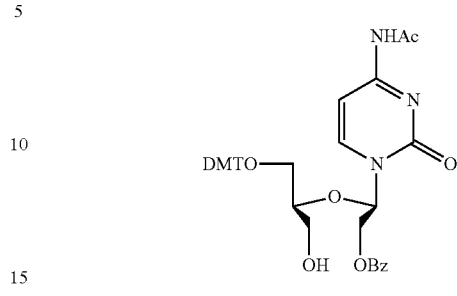

Nucleoside 102-C (3.03 g, 5.14 mmol) was coevaporated with an. toluene (2×30 mL) and dried for 12 h in vacuo. The resulting residue was dissolved in an. DCM (150 mL) along with an. DBU (1.5 mL, 10.3 mmol) and the resulting mixture was cooled to −70° C. Benzoyl chloride (6.56 mL, 5.65 mmol) was slowly added to the reaction mixture. The reaction mixture was stirred for 1 h at −70° C. and subsequently allowed to reach rt whereupon EtOH (4 mL) was added. The reaction mixture was washed with sat. aq. NaHCO$_3$ (2×150 mL). The organic phases were combined and evaporated. The resulting residue was purified by column chromatography (0-5% MeOH in CHCl$_3$) affording product nucleoside 103-C as a white foam after evaporation of the solvents.

Yield: 2.08 g (64%).

R$_f$: 0.24 (5% MeOH in CHCl$_3$).

$^1$H NMR (DMSO-d$_6$): δ 10.97 (s, 1H, NH), 8.25 (d, 1H, Cytidine CH), 7.91 (d, 2H, Ar), 7.65 (ap. t, 1H, Ar) 7.32-7.12 (m, 12H, Ar/Cytidine CH), 6.83 (d, 4H, Ar), 6.34 (t, 1H, H1'), 4.84 (t, 1H, 3'OH), 4.58 (dq, 2H, H2'), 3.74 (s, 6H, 2×—OCH$_3$), 3.70-3.64 (m, 1H, H4'), 3.48 (m, 2H, H3'), 3.07 (m, 2H, H5'), 2.14 (s, 3H, —CH$_3$).

$^{13}$C NMR (DMSO-d$_6$): δ 171.0, 165.0, 162.5, 157.1, 145.5 (Cytidine C5/C6), 144.6, 135.48, .133.6, 129.6 (Ar), 128.8 (Ar), 127.7 (Ar), 127.6 (Ar), 126.6 (Ar), 113.1 (Ar), 95.8 (Cytidine C5/C6), 85.6, 82.0 (C1'), 79.6 (C4'), 79.2 63.9 (C2'), 63.7, 60.5 (C3'), 54.9 (—OCH$_3$), 24.3 (—CH$_3$).

ESI-HiRes (mNa$^+$): m/z: 716.2589 calc.: 716.2759.

4-N-Acetyl-2'-O-benzoyl-3'-O-(2-cyanoethoxy(diisopropylamino)phosphino)-5'-O-(4,4'-dimethoxytrityl)-2',3'-secocytidine (104-C)

Nucleoside 103-C (1.49 g, 2.15 mmol) was coevaporated with an. MeCN (2×20 mL). The residue was dissolved in 20% DIPEA in MeCN (20 mL) and the mixture was stirred. 2-Cyanoethyl-N,N-diisopropylchlorophosphoramidite [P(Cl)(OCH$_2$CH$_2$CN)(N(iPr)$_2$); 0.8 mL] was added to the mixture and stirring was continued for 40 min. Additional 2-cyanoethyl-N,N-diisopropylchlorophosphoramidite (0.4 mL) was added and stirring was continued for 3 h. EtOH (5 mL) was added and the resulting mixture was washed with sat. aq. NaHCO$_3$ (3×50 mL) and the aqueous phase was back-extracted with DCM (50 mL). The organic phases were pooled and evaporated. The residue was purified by column chromatography (0-100% EtOAc in petroleum ether) to afford nucleoside 104-C as a white foam after evaporation of the solvents.

Yield: 940 mg (44%).
R$_f$: 0.42 (5% MeOH in DCM).
$^{31}$P NMR (MeCN): δ 148.8.
ESI-HiRes (mNa$^+$): m/z: 916.3622 calc.: 916.3657.

5'-O-(4,4'-Dimethoxytrityl)-2-N-isobutyryl-2',3'-secoguanosine (102-G)

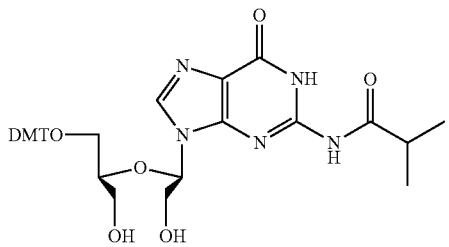

2-N-Isobutyrylguanosine (11.68 g, 17.8 mmol) was coevaporated with an. pyr (50 mL). The resulting residue was dissolved in an. pyr (100 mL). DMT-Cl (4,4'-dimethoxytritylchloride; 7.26 g, 21.46 mmol) was added as a solid material and the reaction mixture was stirred for 1 h at rt. DMAP (50 mg, 0.40 mmol) was added and the resulting mixture was stirred for additional 12 h. The reaction mixture was then washed with sat. aq. NaHCO$_3$ (3×50 mL) and the organic phase evaporated to yield a white foam. This residue was dissolved in dioxane (250 mL) and water (50 mL). NaIO$_4$ (4.57 g, 21.3 mmol) was dissolved in water (50 mL) and was added to the dissolved nucleoside. The mixture was stirred for 1 h during which time a white precipitate was formed. Additional 200 mL dioxane was added and stirring was continued for 15 min. The precipitate was filtered of and washed with dioxane (100 mL). The filtrates were collected and NaBH$_4$ (748 mg, 19.77 mmol) was added and the resulting mixture was stirred for 30 min at rt. To neutralize a buffer (10 mL, 1:1—AcOH:pyridine) was added until pH 7 was reached. The volume of the resulting mixture was reduced to 150 mL and extraction was performed using EtOAc (150 mL). The organic phase was washed with sat. aq. NaHCO$_3$ (3×100 mL) and evaporated, and the residue was purified by column chromatography using a gradient of 0-10% (1:1 MeOH:i-PrOH) in DCM to yield the product as a white solid material after evaporation of the solvents.

Yield: 8.02 g (68%).
R$_f$: 0.24 (7% MeOH in CH$_2$Cl$_2$).
$^{13}$C NMR (DMSO-d$_6$): δ 180.2, 157.9, 154.9, 147.8, 144.7, 135.4, 129.3 (Ar), 127.5 (Ar), 127.4 (Ar), 126.4 (Ar), 120.4, 113.0 (Ar), 85.2, 85.1 (C1'), 79.9 (C4'), 63.5 (C5'), 61.7 (C2'), 61.1 (C3'), 54.9 (—OCH$_3$), 34.7 (quaternary i-Pr), 18.9 (i-Pr), 18.8 (i-Pr).
MALDI-HiRes (mNa$^+$): m/z: 680.2679 calc.: 680.2691.

2'-O-Benzoyl-5'-O-(4,4'-dimethoxytrityl)-2-N-isobutyryl-2',3'-secoguanosine (103-G)

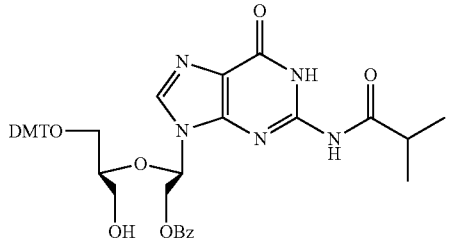

Nucleoside 102-G was suspended in an. toluene (2×30 mL) and evaporated. The resulting residue was dried for 12 h in vacuo. The residue was dissolved in an. DCM (100 mL) along with an. DBU (0.9 mL, 6.1 mmol) and the resulting mixture was cooled to –70° C. Benzoyl chloride (390 μL, 3.36 mmol) was slowly added to the reaction mixture. The reaction mixture was stirred for 1 h at –70° C. and subsequently allowed to reach rt whereupon EtOH (4 mL) was added. The resulting mixture was washed with sat. aq. NaHCO$_3$ (2×100 mL), and the organic phases were combined and evaporated. The resulting residue was purified by column chromatography (0-5% MeOH in CHCl$_3$) affording nucleoside 103-G as a white foam after evaporation of the solvents.

Yield: 1.49 g (63%).
R$_f$: 0.47 (7% MeOH in CH$_2$Cl$_2$).
$^1$H NMR (DMSO-d$_6$): δ 12.10 (s, 1H, NH), 11.72 (s, 1H, NH), 8.32 (s, 1H, guanidine H8), 7.85-7.79 (m, 2H, Ar), 7.65-7.63 (m, 1H, Ar), 7.51-7.45 (m, 2H, Ar), 7.26-6.97 (m, 11H, Ar), 6.79 (m, 4H, Ar), 6.18 (t, 1H, H1'), 5.04-4.82 (m, 3H, H2'/3'OH), 3.82 (m, 1H, H4'), 3.72 (s, 6H, 2×—OCH$_3$), 3.49 (t, 2H, H3'), 3.03-2.74 (m, 3H, H5'/quaternary i-Pr), 1.11 (ap. t, 6H, 2×—CH$_3$).
$^{13}$C NMR (DMSO-d$_6$): δ 180.1, 164.9, 157.8, 154.8, 148.6, 147.9, 144.6, 138.4, 135.5, 135.3, 133.6, 129.3 (Ar), 129.0 (ar), 128.8 (ar), 128.7 (ar), 127.6 (ar), 127.4 (ar), 126.3 (ar), 120.6, 112.9 (ar), 85.1, 82.0 (C1'), 80.1 (C4'), 63.7, 63.3 (C5'), 61.0 (C3'), 54.8 (—OCH$_3$), 34.6 (quaternary i-Pr), 18.8 (—CH$_3$), 18.6 (—CH$_3$).
ESI-HiRes (mNa$^+$): m/z: 784.2943 calc.: 784.2953.

2'-O-Benzoyl-3'-O-(2-cyanoethoxy(diisopropylamino)phosphino)-5'-O-(4,4'-dimethoxytrityl)-2-N-isobutyryl-2',3'-secoguanosine (104-G)

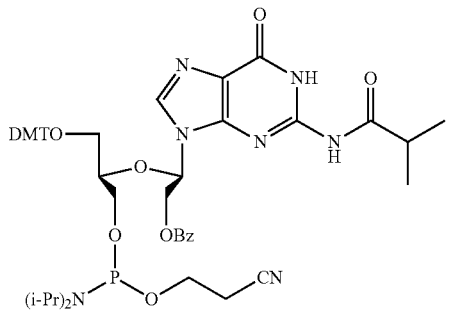

Nucleoside 103-G (1.45 g, 1.9 mmol) was coevaporated with an. MeCN (2×20 mL). The residue was dissolved in 20%

DIPEA in MeCN (20 mL) and the resulting mixture was stirred. 2-Cyanoethyl-N,N-diisopropylchlorophosphoramidite [P(Cl)(OCH$_2$CH$_2$CN)(N(iPr)$_2$); 0.65 mL] was added to the reaction mixture and stirring was continued for 40 min. EtOH (5 mL) was added and the resulting mixture was washed with sat. aq. NaHCO$_3$ (3×50 mL), and the aqueous phase was back-extracted with DCM (50 mL). The organic phases were pooled and evaporated. The residue was precipitated from petroleum ether from a solution in EtOAc to furnish amidite 104-G as a white solid material after drying.

Yield: 607 mg (33%).
R$_f$: 0.3 (1:3 Acetone:toluene).
$^{31}$P NMR (MeCN): δ 148.6.
ESI-HiRes (mNa$^+$): m/z: 984.4028 calc.: 984.4031.

Example 12

Synthesis of Piperazino-Functionalised Monomeric Building Blocks

The example describes procedures that have been conducted in order to exemplify synthesis of monomeric amidite building blocks having an amino functionality attached at the C2'-position of a monomer, i.e. synthesis of the C2'-piperazino-functionalised monomeric building block 111 (Amidite J; base=uracil) starting from nucleoside 103-U via compounds 105, 106, 107, 108, 109 and 110.

2'-O-Benzoyl-3'-O-tert-butyldimethelsilyl-5'-O-(4,4'-dimethoxytrityl)-2',3'-secouridine (105)

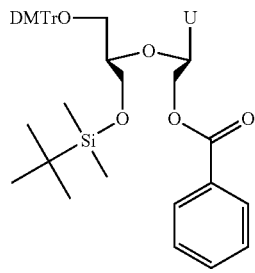

Nucleoside 103-U (328 mg, 0.50 mmol) was dissolved in an. pyridine (2 mL) and stirred at rt. TBDMSCl (113 mg, 0.75 mmol) was added to the reaction mixture that was stirred for 19 h. Water (1 mL) was then added and stirring was continued for additional 15 min whereupon the reaction mixture was diluted with DCM (50 mL) and washed with sat. aq. NaHCO$_3$ (2×25 mL) and brine (25 mL). The organic phase was dried over Na$_2$SO$_4$, filtered and evaporated to dryness under reduced pressure. The residue was purified by silica gel column chromatography using MeOH (0-8%) in DCM as eluent thus affording nucleoside 105 as a white solid material. Yield 294 mg (78%). $^1$H NMR (300 MHz, DMSO-d$_6$) δ 11.46 (s, 1H, NH), 7.95-7.79 (m, 3H), 7.71-7.63 (m, 1H), 7.57-7.48 (m, 2H), 7.37-7.13 (m, 9H), 6.84 (d, J=8.8 Hz, 4H), 6.22 (t, J=5.7 Hz, 1H, H1'), 5.58 (d, J=8.0 Hz, 1H, H5), 4.69-4.45 (m, 2H, H2'), 3.80-3.64 (m, 8H, 2×OMe and H4'), 3.54 (t, J=4.7 Hz, 1H, H3'), 3.09-2.97 (m, 2H, H5'), 0.73 (s, 9H, 3×Me), −0.07 and −0.09 (2×s, 6H, 2×Me). $^{13}$C NMR (75.5 MHz, DMSO-d$_6$): δ 165.0, 163.1, 158.0, 151.1, 144.7, 140.6, 135.5, 135.4, 133.7, 129.6, 129.1, 129.0, 128.8, 127.8, 127.6, 126.6, 113.1, 102.3, 85.5, 81.1, 79.2, 63.4, 63.1, 62.1, 55.0, 25.6, 17.7, 2×−5.7. ESI-HRMS: m/z 789.3147 ([M+Na]$^+$, C$_{43}$H$_{50}$N$_2$O$_9$Si.Na calc. 789.3178).

3'-O-tert-Butyldimethelsilyl-5'-O-(4,4'-dimethoxytrityl)-2',3'-secouridine (106)

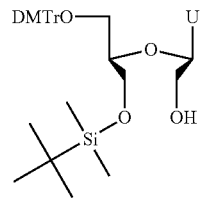

NaOH (845 mg, 21.1 mmol) was mixed with an. MeOH (200 mL) and the resulting mixture was cooled to 0° C. Nucleoside 105 (3.10 g, 4.05 mmol) was dissolved in an. MeOH (40 mL) and the resulting mixture was added to the above mixture and the resulting reaction mixture was stirred for 2.5 h. Sat. aq. NH$_4$Cl (10 mL) was added and stirring was continued for additional 10 min whereupon water (100 mL) was added and extraction was performed using DCM (4×200 mL). The organic phase was evaporated to dryness under reduced pressure and the residue then co-evaporated with an. pyridine (10 mL). The residue was purified by silica gel column chromatography using MeOH (5-10%) in DCM as eluent thus affording nucleoside 106 as a white solid material. Yield 2.54 g (95%). $^1$H NMR (300 MHz, DMSO-d$_6$): δ 11.35 (s, 1H, NH), 7.66 (d, J=7.6 Hz, 1H, H6), 7.33-7.14 (m, 9H), 6.88-6.82 (m, 4H), 5.82 (t, J=6.0 Hz, 1H, H1'), 5.53 (d, J=8 Hz, 1H, H5), 5.11 (t, J=5.8 Hz, 1H, 2'-OH), 3.73 (s, 6H, 2×OMe), 3.69-3.45 (m, 5H, H2', H4' and H3'), 3.01-2.93 (m, 2H, H5'), 0.76 (s, 9H, 3×Me), −0.03 and −0.05 (2×s, 6H, 2×Me). $^{13}$C NMR (75.5 MHz, DMSO-d$_6$): δ 163.2, 158.0, 151.6, 144.8, 135.6, 135.4, 129.6, 127.7, 127.6, 126.6, 113.1, 101.8, 85.4, 83.5, 78.5, 63.3, 61.8, 61.0, 55.0, 25.6, 17.7, 2×−5.6. ESI-HRMS: m/z 685.2885 ([M+Na]$^+$, C$_{36}$H$_{46}$N$_2$O$_8$Si.Na calc. 685.2916).

3'-O-tert-Butyldimethylsilyl-5'-O-(4,4'-dimethoxytrityl)-2'-O-methanesulfonyl-2',3'-secouridine (107)

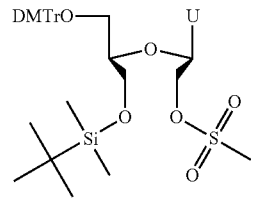

Nucleoside 106 (927 mg, 1.40 mmol) was dissolved in an. pyridine (20 mL) and the resulting mixture was stirred at 0° C. MsCl (220 μL, 2.83 mmol) was added dropwise and the resulting mixture was stirred for 3 h at rt. EtOH (2 mL) was added and stirring was continued for additional 10 min. The mixture was then evaporated to dryness and the residue was purified by silica gel column chromatography using MeOH (0-7%) in DCM as eluent thus affording nucleoside 107 as a white foam. Yield 834 mg (81%). $^1$H NMR (300 MHz, DMSO-d$_6$): δ 11.49 (s, 1H, NH), 7.77 (d, J=8.2 Hz, 1H, H6), 7.35-7.14 (m, 9H), 6.86 (d, J=8.5 Hz, 4H), 6.11 (t, J=5.7 Hz, 1H, H1'), 5.60 (d, J=8.1 Hz, 1H, H5), 4.49 (d, J=5.5 Hz, 2H, H2'), 3.77-3.48 (m, 9H, 2×OMe, H4' and H3'), 3.22 (s, 3H, Me), 3.10-2.89 (m, 2H, H5'), 0.77 (s, 9H, 3×Me), −0.02 and −0.04 (2×s, 6H, 2×Me). $^{13}$C NMR (75.5 MHz, DMSO-d$_6$): δ 163.1, 158.0, 151.7, 144.7, 140.5, 135.5, 135.3, 129.6, 127.8, 127.6, 126.6, 113.1, 102.4, 85.5, 80.6, 79.1, 67.8, 63.1, 61.8, 55.0, 36.8, 25.6, 17.7, −5.6, −5.7. ESI-HRMS: m/z 763.2662 ([M+Na]$^+$, C$_{37}$H$_{48}$N$_2$O$_{10}$Ssi.Na calc. 763.2692).

3'-O-tert-butyldimethylsilyl-2'-deoxy-5'-O-(4,4'-dimethoxytrityl)-2'-piperazino-2',3'-secouridine (108)

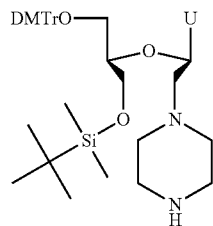

Nucleoside 107 (276 mg, 0.373 mmol) was dissolved in an. pyridine (3 mL) and piperazine (3.21 g, 37.3 mmol) was added under stirring at rt. The reaction mixture was then heated to 150° C. and stirred for 1 h followed by cooling to rt. The reaction mixture was diluted with sat. aq. NaHCO$_3$ (200 mL) whereupon extraction was performed using chloroform (7×100 mL). The organic phase was dried over Na$_2$SO$_4$, filtered and evaporated to dryness. The residue was purified by silica gel column chromatography using first MeOH (0-5%) in DCM and then half sat. methanolic ammonia (5%) in DCM as eluent systems thus affording nucleoside 108 as a white solid material. Yield 182 mg (67%). $^1$H NMR (300 MHz, DMSO-d$_6$): δ 7.64 (d, J=8.1 Hz, 1H, H6), 7.34-7.13 (m, 9H), 6.85 (d, J=7.8 Hz, 4H), 5.98 (t, J=6.0 Hz, 1H, H1'), 5.53 (d, J=8.1 Hz, 1H, H5), 3.72 (s, 6H, 2×OMe), 3.68-3.51 (m, 3H, H4' and H3'), 3.04-2.90 (m, 2H, H5'), 2.77-2.54 (m, 6H, H2', piperazino), 2.48-2.27 (m, 4H, piperazino), 0.77, (s, 9H, 3×Me), −0.02 and −0.04 (2×s, 6H, 2×Me). $^{13}$C NMR (75.5 MHz, DMSO-d$_6$): δ 163.2, 158.0, 151.3, 144.8, 141.1 (C6), 135.6, 135.4, 129.5, 127.7, 127.6, 126.6, 113.1, 113.1, 101.8 (C5), 85.4, 81.3 (C1'), 78.3, 63.1, 62.1, 60.1, 55.0 (OMe), 55.0 (OMe), 53.8, 45.3, 25.7 (Me), 17.8, −5.5 (Me), −5.6 (Me). ESI-HRMS: m/z 731.3859 ([M+H]$^+$, C$_{40}$H$_{54}$N$_4$O$_7$Si.H calc. 731.3834).

3'-O-tert-Butyldimethylsilyl-2'-deoxy-5'-O-(4,4'-dimethoxytrityl)-2'-(4-N-trifluoroacetyl)piperazino-2',3'-secouridine (109)

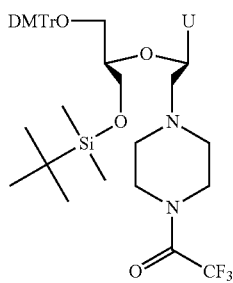

Nucleoside 108 (102 mg, 0.14 mmol) was dissolved in an. MeOH (2 mL) and the resulting mixture was stirred at rt. DMAP (10 mg, 0.08 mmol) and ethyl trifluoroacetate (22 μL, 0.184 mmol) were added and stirring was continued for 16 h. The mixture was then evaporated to dryness under reduced pressure and the residue was purified by silica gel column chromatography using MeOH (0-2%) in DCM as eluent thus affording nucleoside 109 as a white solid material. Yield 100 mg (86%). $^1$H NMR (300 MHz, DMSO-d$_6$): δ 11.37 (s, 1H, NH), 7.66 (d, J=7.8 Hz, 1H, H6), 7.38-7.12 (m, 9H), 6.93-6.80 (m, 4H), 6.00 (t, J=5.9 Hz, 1H, H1'), 5.54 (d, J=7.8 Hz, 1H, H5), 3.73 (s, 6H, 2×OMe), 3.70-3.40 (m, 7H, H3', H4' and piperazino), 3.08-2.92 (m, 2H, H5'), 2.90-2.52 (m, 6H, H2' and piperazino), 0.77 (s, 9H, 3×Me), 0.00 and −0.04 (2×s, 6H, 2×Me). $^{13}$C NMR (75.5 MHz, DMSO-d$_6$): δ 163.2, 158.0, 151.3, 144.8, 140.8, 135.6, 135.4, 129.5, 127.7, 127.6, 126.6, 113.1, 102.0, 85.5, 81.0, 78.2, 63.1, 62.0, 58.9, 55.0, 52.6, 52.0, 45.4, 43.0, 25.6, 17.8, −5.6, −5.6. ESI-HRMS: m/z 849.3452 ([M+Na]$^+$, C$_{42}$H$_{53}$F$_3$N$_4$O$_8$Si.Na calc. 849.3477).

2'-Deoxy-5'-O-(4,4'-dimethoxytrityl)-2'-(N-trifluoroacetyl)piperazino-2',3'-secouridine (110)

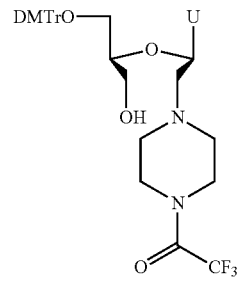

Nucleoside 109 (251 mg, 0.304 mmol) was co-evaporated with an. THF (2×5 mL) and then dissolved in an. THF (10 mL). 1M TBAF in THF (606 μL, 0.606 mmol) was added dropwise under stirring to this mixture at rt during 1 h and stirring at rt was then continued for 21 h. The reaction mixture was evaporated to dryness under reduced pressure and the residue then dissolved in EtOAc (40 mL). The resulting mixture was washed with sat. aq. NaHCO$_3$ (3×10 mL) and water (3×10 mL), and the separated organic phase was dried over Na$_2$SO$_4$, filtered and evaporated to dryness under reduced pressure. The residue was purified by silica gel column chromatography using EtOAc (60-100%) in petroleum ether as eluent thus affording nucleoside 110 as a white solid material. Yield 111 mg (51%). $^1$H NMR (300 MHz, DMSO-d$_6$): δ 11.36 (s, 1H, NH), 7.66 (d, J=8.1 Hz, 1H, H6), 7.34-7.27 (m, 4H), 7.24-7.14 (m, 5H), 6.92-6.82 (m, 4H), 5.98 (t, J=6.1 Hz, 1H, H1'), 5.53 (d, J=7.3 Hz, 1H, H5), 4.80 (t, J=5.3 Hz, 1H, 3'-OH), 3.73 (s, 6H, 2×OMe), 3.63-3.38 (m, 8H, H4', H3' and piperazino), 3.07-2.89 (m, 2H, H5'), 2.77 (t, J=5.8 Hz, 2H, H2'), 2.66-2.54 (m, 3H, piperazino). $^{13}$C NMR (75.5 MHz, DMSO-d$_6$): δ 163.2, 158.0, 151.2, 144.8, 140.9, 135.6, 135.5, 129.6, 129.6, 127.8, 127.6, 126.6, 113.1, 101.9, 85.4, 81.3, 79.2, 63.5, 60.7, 59.1, 55.0, 52.7, 52.1, 45.4, 42.9. ESI-HRMS: m/z 735.2585 ([M+Na]$^+$, C$_{36}$H$_{39}$F$_3$N$_4$O$_8$.Na calc. 735.2612).

3'-(2-Cyanoethoxy(diisopropylamino)phosphino)-2'-deoxy-5'-O-(4,4'-dimethoxytrityl)-2'-(N-trifluoroacetyl)piperazino-2',3'-secouridine (111)

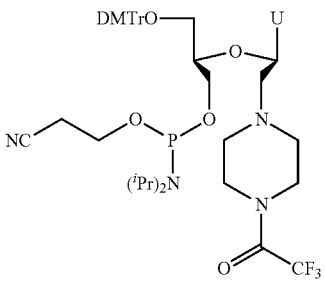

Nucleoside 110 (91 mg, 0.128 mmol) was co-evaporated with an. DCM (2×5 mL) and then dissolved in an. DCM (2.5 mL). DIPEA (111 μL, 0.64 mol) was added under stirring to this mixture at rt whereupon 2-cyanoethyl N,N-diisopropylphosphoramidochloriditite (57 μL, 0.256 mmol) was added dropwise. Stirring at rt was continued for 1 h, whereupon EtOH (0.5 mL) was added followed by stirring for additional 10 min. DCM (40 mL) was added followed by washing with sat. aq. NaHCO$_3$ (20 mL). The separated organic phase was dried over Na$_2$SO$_4$, filtered and evaporated to dryness under reduced pressure. The residue was purified by silica gel column chromatography using EtOAc (60-80%) in petroleum ether as eluent thus affording the amidite 111 as a white solid material. Yield 106 mg (91%). $^{31}$P NMR (CDCl$_3$) δ 150.0 and 149.5. ESI-HRMS: m/z 913.3841 ([M+H]$^+$, C$_{45}$H$_{56}$F$_3$N$_6$O$_9$P.H calc. 913.3871).

Example 13

Synthesis of Oligonucleotides Containing Piperazino-Functionalised Monomeric Building Blocks By using methods described in Example 1, efficient incorporation of monomer J with a free terminal NH in the piperazino moiety was accomplished using RNA amidites and amidite 111. The coupling yields of this amidite were above 95%.

---

The invention claimed is:

1. An oligomer comprising an acyclic 2'-3'-seco-nucleomonomer, wherein the oligomer is a microRNA, wherein the oligomer comprises from one to five acyclic monomers, and wherein the acyclic monomer is monomer D

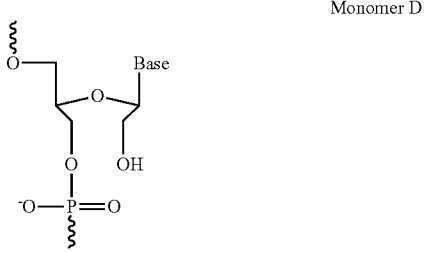

Monomer D wherein Base is a nucleobase.

2. The oligomer of claim 1, further comprising a nucleotide analogue selected from the group consisting of 2'-O-alkyl-RNA monomers, 2'-amino-DNA monomers, 2'-fluoro-DNA monomers, PNA monomers, HNA monomers, ANA monomers, FANA monomers, CeNA monomers, ENA monomers, DNA monomers, and INA monomers.

3. The oligomer of claim 1, further comprising one or more 2'-O-alkyl-RNA nucleotide analogues.

4. The oligomer of claim 1, further comprising a phosphorothioate linkage or a boranophosphate linkage.

5. The oligomer of claim 1, wherein the oligomer has a sequence that is complementary to a target nucleotide sequence.

6. The oligomer of claim 1, wherein the oligomer has reduced off-target effects as compared to an oligonucleotide having the same sequence with natural RNA monomers instead of acyclic monomers.

7. The oligomer of claim 1, wherein the oligomer has increased or prolonged potency for gene silencing as compared to an oligonucleotide having the same sequence with natural RNA monomers instead of acyclic monomers.

8. The oligomer of claim 1, wherein the oligomer has improved stability towards enzymatic degradation as compared to an oligonucleotide having the same sequence with natural RNA monomers instead of acyclic monomers.

9. The oligomer of claim 1, wherein the oligomer has reduced immune stimulation as compared to an oligonucleotide having the same sequence with natural RNA monomers instead of acyclic monomers.

* * * * *